(12) United States Patent
Sagisaka et al.

(10) Patent No.: US 11,053,267 B2
(45) Date of Patent: Jul. 6, 2021

(54) ELECTROCHROMIC COMPOUND, ELECTROCHROMIC COMPOSITION, AND DISPLAY ELEMENT

(71) Applicants: Toshiya Sagisaka, Kanagawa (JP); Hiroyuki Takahashi, Kanagawa (JP); Takashi Okada, Kanagawa (JP); Shigenobu Hirano, Kanagawa (JP); Tohru Yashiro, Kanagawa (JP); Koh Fujimura, Tokyo (JP); Yoshihisa Naijo, Kanagawa (JP); Yoshinori Okada, Kanagawa (JP); Kazuaki Tsuji, Kanagawa (JP); Sukchan Kim, Kanagawa (JP); Keiichiroh Yutani, Kanagawa (JP); Tamotsu Horiuchi, Shizuoka (JP); Mamiko Inoue, Tokyo (JP)

(72) Inventors: Toshiya Sagisaka, Kanagawa (JP); Hiroyuki Takahashi, Kanagawa (JP); Takashi Okada, Kanagawa (JP); Shigenobu Hirano, Kanagawa (JP); Tohru Yashiro, Kanagawa (JP); Koh Fujimura, Tokyo (JP); Yoshihisa Naijo, Kanagawa (JP); Yoshinori Okada, Kanagawa (JP); Kazuaki Tsuji, Kanagawa (JP); Sukchan Kim, Kanagawa (JP); Keiichiroh Yutani, Kanagawa (JP); Tamotsu Horiuchi, Shizuoka (JP); Mamiko Inoue, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 16/819,377

(22) Filed: Mar. 16, 2020

(65) Prior Publication Data
US 2020/0216478 A1 Jul. 9, 2020

Related U.S. Application Data

(62) Division of application No. 16/122,452, filed on Sep. 5, 2018, now Pat. No. 10,626,133, which is a division (Continued)

(30) Foreign Application Priority Data

Nov. 1, 2012 (JP) .................................. 2012-241679
May 1, 2013 (JP) .................................. 2013-096261

(51) Int. Cl.
*C07D 401/10* (2006.01)
*C07D 401/14* (2006.01)
(Continued)

(52) U.S. Cl.
CPC ........ *C07F 9/65583* (2013.01); *C07D 401/10* (2013.01); *C07D 401/14* (2013.01);
(Continued)

(58) Field of Classification Search
CPC ........................ C07D 401/14; C07D 401/10
See application file for complete search history.

(56) References Cited

U.S. PATENT DOCUMENTS 6,301,038 B1 10/2001 Fitzmaurice et al.
7,166,689 B2 1/2007 Sagisaka et al.
(Continued)

FOREIGN PATENT DOCUMENTS

CN 102082232 6/2011
JP 2000-314860 11/2000
(Continued)

OTHER PUBLICATIONS

International Search Report dated Feb. 10, 2014 for counterpart International Patent Application No. PCT/JP2013/080363 filed Nov. 1, 2013.
(Continued)

*Primary Examiner* — Brian E McDowell
(74) *Attorney, Agent, or Firm* — Oblon, McClelland, Maier & Neustadt, L.L.P.

(57) ABSTRACT

To provide an electrochromic compound, represented by the following general formula (I):

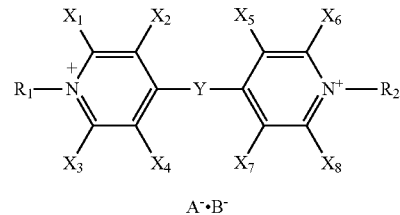

General Formula (I)

where $X_1$, $X_2$, $X_3$, $X_4$, $X_5$, $X_6$, $X_7$ and $X_8$ are each independently a hydrogen atom or a monovalent substituent; $R_1$ and $R_2$ are each independently a monovalent substituent; $A^-$ and $B^-$ are each independently a monovalent anion; and Y is represented by the following general formula (II) or (III):

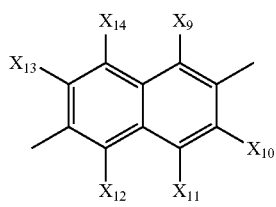

General Formula (II)

(Continued)

-continued

General Formula (III)

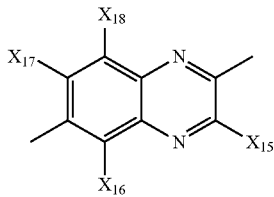

where $X_9$, $X_{10}$, $X_{11}$, $X_{12}$, $X_{13}$, $X_{14}$, $X_{15}$, $X_{16}$, $X_{17}$, and $X_{18}$ are each independently a hydrogen atom or a monovalent substituent.

14 Claims, 8 Drawing Sheets

Related U.S. Application Data of application No. 14/433,176, filed as application No. PCT/JP2013/080363 on Nov. 1, 2013, now Pat. No. 10,093,693.

(51) Int. Cl.
   C07F 9/6558 (2006.01)
   C07F 9/58 (2006.01)
   G02F 1/1503 (2019.01)
   C07F 7/08 (2006.01)
   C09K 9/02 (2006.01)

(52) U.S. Cl.
   CPC .............. *C07F 7/0836* (2013.01); *C07F 9/58* (2013.01); *C09K 9/02* (2013.01); *G02F 1/1503* (2019.01); *C09K 2211/1007* (2013.01); *C09K 2211/1011* (2013.01); *C09K 2211/1029* (2013.01); *C09K 2211/1044* (2013.01); *G02F 2203/02* (2013.01)

(56) References Cited

U.S. PATENT DOCUMENTS

| 7,816,674 | B2 | 10/2010 | Kato et al. |
| 2002/0167480 | A1 | 11/2002 | Johnson et al. |
| 2005/0012977 | A1 | 1/2005 | Mizuno |
| 2006/0110638 | A1 | 5/2006 | Corr et al. |
| 2007/0092760 | A1 | 4/2007 | Sagisaka et al. |
| 2008/0112033 | A1 | 5/2008 | Shibuya et al. |
| 2009/0230386 | A1 | 9/2009 | Yamamoto et al. |
| 2009/0321727 | A1 | 12/2009 | Yutani et al. |
| 2010/0193775 | A1 | 8/2010 | Yutani et al. |
| 2010/0219405 | A1 | 9/2010 | Sagisaka et al. |
| 2011/0040107 | A1 | 2/2011 | Goto et al. |
| 2011/0222139 | A1 | 9/2011 | Naijo et al. |
| 2012/0050838 | A1 | 3/2012 | Hirano et al. |
| 2012/0119195 | A1 | 5/2012 | Sagisaka et al. |
| 2012/0153271 | A1 | 6/2012 | Goto et al. |
| 2012/0154892 | A1 | 6/2012 | Yashiro et al. |
| 2012/0194894 | A1 | 8/2012 | Yashiro et al. |

FOREIGN PATENT DOCUMENTS

| JP | 2001-510590 | 7/2001 |
| JP | 3237282 | 12/2001 |
| JP | 2003-121883 | 4/2003 |
| JP | 2003-161964 | 6/2003 |
| JP | 2003-270671 | 9/2003 |
| JP | 2004-151265 | 5/2004 |
| JP | 2004-520621 | 7/2004 |
| JP | 2004-361514 | 12/2004 |
| JP | 2004-536344 | 12/2004 |
| JP | 2006-071767 | 3/2006 |
| JP | 2006-106669 | 4/2006 |
| JP | 2006-519222 | 8/2006 |
| JP | 2006-283613 | 10/2006 |
| JP | 2007-171781 | 7/2007 |
| JP | 2008-122578 | 5/2008 |
| JP | 2010-033016 | 2/2010 |
| JP | 2010-116483 | 5/2010 |
| JP | 2011-102382 | 5/2011 |
| JP | 2011-209688 | 10/2011 |
| JP | 2011-257474 | 12/2011 |
| JP | 2012-141584 | 7/2012 |
| JP | 2012-224548 | 11/2012 |
| WO | WO 03/009059 A1 | 1/2003 |

OTHER PUBLICATIONS

Extended European Search Report dated Oct. 14, 2015 in European Patent application No. 13852185.1.

ELECTROCHROMIC COMPOUND, ELECTROCHROMIC COMPOSITION, AND DISPLAY ELEMENT

This is a divisional of application Ser. No. 16/122,452, filed Sep. 5, 2018, which is a divisional of application Ser. No. 14/433,176, filed Apr. 2, 2015, which is the National Stage of International application no. PCT/JP2013/080363, filed Nov. 1, 2013 which claimed priority to Japanese patent application nos. 2012-241679, filed Nov. 1, 2012, and 2013-096261, filed May 1, 2013, of which all of the disclosures are incorporated herein by reference in their entireties

TECHNICAL FIELD

The present invention relates to an electrochromic compound, and an electrochromic composition, both of which colors in cyan as they are colored, and relates to a display element using the electrochromic compound or the electrochromic composition.

BACKGROUND ART

As for an electronic medium replacing paper, developments of electronic paper have been recently actively carried out.

The electronic paper has characteristics that the display device thereof is used like paper, and therefore requires properties different from conventional display devices, such as CRT and LCD. For example, required properties thereof are being a reflective a display device as well as having high white reflectance and high contrast ratio, being able to display with high definition, giving the display a memory function, being driven at low voltage, being thin and light, and being inexpensive. Among them, as properties associated with a quality of a display, particularly white reflectivity and contrast ratio close to that of paper, and color display are highly demanded.

Previously, as for a display device for use as electronic paper, for example, proposed are a system using reflecting liquid crystals, a system using electrophoresis, a system using toner migration, and the like. In any of these systems, however, it is very difficult to perform multicolor display with maintaining white reflectivity and contrast ratio. In order to perform multicolor display, color filters are typically provided. When color filters are provided, the color filters themselves absorb light to thereby reduce reflectance. Moreover, use of the color filters requires to divide one pixel into three, red (R), green (G), and blue (B), reflectance of a display device reduces. Along the reduction in the reflectance of the display device, the contrast ratio thereof also reduces. When the white reflectivity and contrast ratio are significantly reduced, the visibility becomes very poor, and therefore it is difficult to use such device as electronic paper.

PTL 1 and PTL 2 each disclose a reflecting color display medium, in an electrophoresis element of which color filters are formed, but it is clear that such display medium cannot provide excellent image quality even when color filters are formed in the display medium of low white reflectivity and a low contrast ratio. Moreover, PTL 3 and PTL 4 each disclose an electrophoresis, with which color display is realized by moving particles, which are tinted in a plurality of colors. Theoretically, use of this method does not lead to a solution for the aforementioned problems, and cannot realize both high white reflectivity and a high contrast ratio.

Meanwhile, as a promising technology for realizing a reflecting display device without providing color filters as described above, there is a system using electrochromic phenomenon. The phenomenon where, as voltage is applied, an oxidation-reduction reaction is reversibly caused depending on the polarity to thereby reversibly change color is called electrochromism. A display device utilizing coloring/bleaching (may also stated as coloring and bleaching hereinafter) of an electrochromic compound which cases this phenomenon is an electrochromic display device. Since this electrochromic display device is a reflecting display device, has a memory effect, and can be driven at low voltage, researches and developments of electrochromic devices have been widely conducted from a development of materials and designing of devices, as a promising option for a display device technology for electronic paper.

However, as the electrochromic display device performs coloring and bleaching using an oxidation-reduction reaction, the electrochromic display device has a disadvantage that a coloring-bleaching response speed is slow. PTL 5 discloses an example, in which an improvement of the coloring-bleaching response speed is attempted by fixing an electrochromic compound adjacent to an electrode. According to the descriptions in PTL 5, although the time required for coloring and bleaching is conventionally about 10 seconds, the time required from colorless to color in blue and the time required from blue to colorless are both improved to about 1 second. However, this is not necessarily sufficient. As for the researches and developments of electrochromic display devices, further improvements of the coloring-bleaching response speed are necessary.

An electrochromic display device can display various colors depending on a structure of an electrochromic compound used as a display material, and therefore it is hoped to be used as a multicolor display device. Especially as the electrochromic display device can reversibly change its colorless state to the color state, a laminate multicolor structure can be realized. In the color display of the laminate structure, it is not necessary to divide one pixel into three, red (R), green (G), and blue (B), as in the conventional technology. Therefore, there are advantages that the reflectance and contrast ratio of the display device are not reduced.

There are several conventional examples of a multicolor display device utilizing such electrochromic display device. For example, PTL 6 discloses a multicolor display device, in which particles of a plurality of electrochromic compounds are laminated. In PTL 6, disclosed is an example of a multicolor display device, in which a plurality of electrochromic compounds, which are high molecular compounds having functional groups, each of which requires different voltage to color, are laminated to form a multicolor display electrochromic compound.

Moreover, PTL 7 discloses a display device, in which multiple electrochromic layers are formed on an electrode to display multiple colors utilizing a difference in voltage or current required for color. In PTL 7, disclosed is an example of a multicolor display device, which colors different colors, and has a display layer formed by laminating or mixing a plurality of electrochromic compounds each require different threshold voltage and electric charge to color.

PTL 8 discloses an electrochromic device in which a full-color display is realized by laminating a plurality of structural units each formed by sandwiching an electrolyte layer containing an electrochromic compound. Moreover, PTL 9 discloses an example of a multicolor display device corresponding to RGB 3 colors, in which a passive matrix panel and active matrix panel are composed of electrochromic elements, in each of which an electrolyte layer containing at least one electrochromic compound is present. Furthermore, PTL 10 discloses that coloring properties and durability are improved by a reversible recording material, in which one, or two or more compounds having the specific structure are contained on surfaces of metal oxide particles. Moreover, PTL 11 discloses an electrochromic compound having a pyridine ring, and represented by the certain structural formula, which can color in yellow and can be bleached. Furthermore, PTL 12 disclosed phthalic acid-based compounds which colors in yellow, magenta, and cyan.

The viologen-based organic electrochromic compounds disclosed in PTL 5, PTL 6, and PTL 7 are compounds having high stability and high durability for repetitive use, but they display colors, such as blue, and green, not 3 primary colors, yellow, magenta, and cyan, required for formation of full color. Moreover, the styryl-based dyes listed in PTL 8, PTL 9, and PTL 10 display excellent yellow, magenta, and cyan, but these dyes have problems in stability of coloring and bleaching, or durability for repetitive use.

Moreover, PTL 11 is related to the compound, which colors in yellow and is bleached, not cyan. The phthalic acid-based compound disclosed in PTL 12 has a problem that such compound has a poor memory function.

As mentioned above, an ideal electrochromic compound for realizing full-color electronic paper has not been provided, and it is desired to provide the material having excellent color tone, durability, and stability.

CITATION LIST

Patent Literature

PTL 1: Japanese Patent Application Laid-Open (JP-A) No. 2003-161964
PTL 2: JP-A No. 2004-361514
PTL 3: JP-A No. 2004-520621
PTL 4: JP-A No. 2004-536344
PTL 5: JP-A No. 2001-510590
PTL 6: JP-A No. 2003-121883
PTL 7: JP-A No. 2006-106669
PTL 8: JP-A No. 2003-270671
PTL 9: JP-A No. 2004-151265
PTL 10: JP-A No. 2008-122578
PTL 11: JP-A No. 2011-102382
PTL 12: JP-A No. 2006-71767

SUMMARY OF INVENTION

Technical Problem

The present invention aims to provide an electrochromic compound, which exhibits sharp light absorption spectrum characteristic as colored, colors in vivid cyan, and exhibits less remained color as bleached.

Solution to Problem

As for the means for solving the aforementioned problems, the electrochromic compound of the present invention is represented by the following general formula (I):

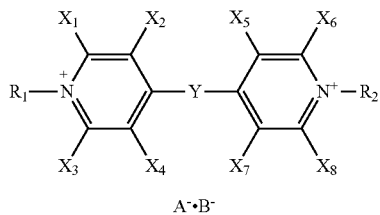

General Formula (I)

where $X_1$, $X_2$, $X_3$, $X_4$, $X_5$, $X_6$, $X_7$ and $X_8$ are each independently a hydrogen atom or a monovalent substituent; $R_1$ and $R_2$ are each independently a monovalent substituent; $A^-$ and $B^-$ are each independently a monovalent anion; and Y is represented by the following general formula (II) or (III):

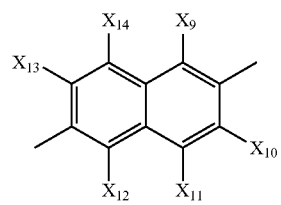

General Formula (II)

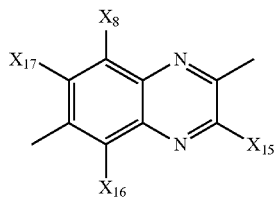

General Formula (III)

where $X_9$, $X_{10}$, $X_{11}$, $X_{12}$, $X_{13}$, $X_{14}$, $X_{15}$, $X_{16}$, $X_{17}$, and $X_{18}$ are each independently a hydrogen atom or a monovalent substituent.

Advantageous Effects of Invention

The present invention can solve the aforementioned various problems in the art, and can provide an electrochromic compound, which exhibits sharp light absorption spectrum characteristic as colored, colors in vivid cyan, and exhibits less remained color as bleached.

DESCRIPTION OF EMBODIMENTS

Electrochromic Compound

Figure 1A:
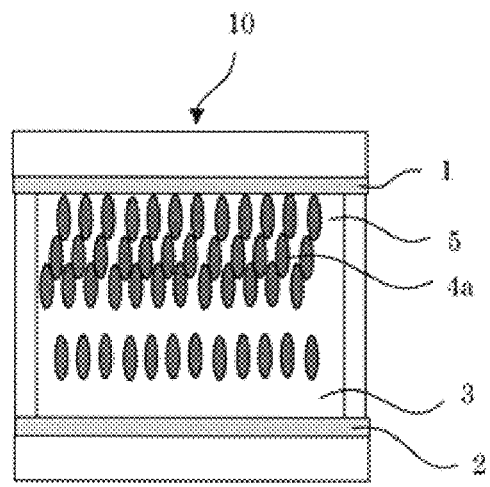
FIG. 1A is a schematic diagram illustrating a structural example of a typical display element using the electrochromic compound of the present invention.

The present inventors have diligently conducted studies to solve the aforementioned problems. As a result, it has found out that the aforementioned problems can be solved with an electrochromic compound represented by the following general formula (I). Specifically, the electrochromic compound represented by the following general formula (I) has sharp light absorption characteristics as colored, colors in cyan, and exhibits less color as bleached.

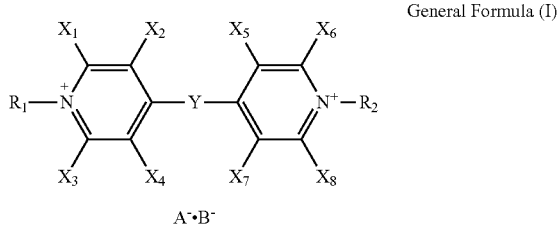

General Formula (I)

In the general formula (I), $X_1$, $X_2$, $X_3$, $X_4$, $X_5$, $X_6$, $X_7$ and $X_8$ are each independently a hydrogen atom or a monovalent substituent; $R_1$ and $R_2$ are each independently a monovalent substituent; $A^-$ and $B^-$ are each independently a monovalent anion; and Y is represented by the following general formula (II) or (III):

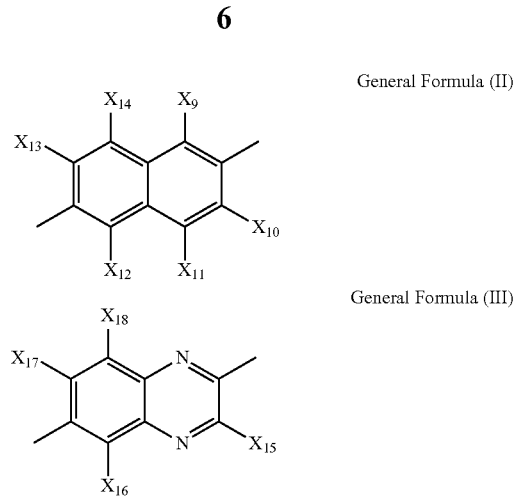

General Formula (II)

General Formula (III)

In the general formulae (II) and (III), $X_9$, $X_{10}$, $X_{11}$, $X_{12}$, $X_{13}$, $X_{14}$, $X_{15}$, $X_{16}$, $X_{17}$, and $X_{18}$ are each independently a hydrogen atom or a monovalent substituent.

In the general formulae (I), (II), and (III), $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, and $X_{18}$ may be a hydrogen atom, a halogen atom, a hydroxyl group, a nitro group, a cyano group, a carboxyl group, a carbonyl group, an alkoxycarbonyl group that may have a substituent, an aryloxycarbonyl group that may have a substituent, an alkylcarbonyl group that may have a substituent, an arylcarbonyl group that may have a substituent, an amide group, an aminocarbonyl group, a monoalkylaminocarbonyl group that may have a substituent, a dialkylaminocarbonyl group that may have a substituent, a monoarylaminocarbonyl group that may have a substituent, a diarylaminocarbonyl group that may have a substituent, a sulfonic acid group, a sulfonyl group, an alkoxysulfonyl group that may have a substituent, an aryloxysulfonyl group that may have a substituent, an alkylsulfonyl group that may have a substituent, an arylsulfonyl group that may have a substituent, a sulfone amide group, an aminosulfonyl group, a monoalkylaminosulfonyl group that may have a substituent, a dialkylaminosulfonyl group that may have a substituent, a monoarylaminosulfonyl group that may have a substituent, a diarylaminosulfonyl group that may have a substituent, an amino group, a monoalkylamino group that may have a substituent, a dialkylamino group that may have a substituent, an alkyl group that may have a substituent, an alkenyl group that may have a substituent, an alkynyl group that may have a substituent, an aryl group that may have a substituent, an alkoxy group that may have a substituent, an aryloxy group that may have a substituent, an alkylthio group that may have a substituent, an arylthio group that may have a substituent, or a heterocyclic group that may have a substituent.

Use of these groups gives a resulting electrochromic compound solubility to a solvent, which makes a production process of an element easy. Moreover, it enables to adjust a color spectrum (color).

In the general formula (I), moreover, monovalent groups represented by $R_1$, and $R_2$ may be each independently an alkyl group that may have a functional group, an alkenyl group that may have a functional group, an alkynyl group that may have a functional group, or an aryl group that may have a functional group.

It is preferred that either $R_1$ or $R_2$, or both thereof have a functional group capable of directly or indirectly bonding to a hydroxyl group. The functional group capable of directly or indirectly bonding to a hydroxyl group is not particularly limited, as long as it is a functional group capable of directly or indirectly bonding to a hydroxyl group through hydrogen bonding, absorption, or a chemical reaction. The structure of such functional group is not limited. Preferable examples thereof include: a phosphonic acid group; a phosphoric acid group; a silyl group (or a silanol group), such as a trichlorosilyl group, a trialkoxysilyl group, a monochlorosilyl group, and a monoalkoxysilyl group; and a carboxyl group.

As for the trialkoxysilyl group, preferred are a triethoxysilyl group, and a trimethoxysilyl group. Among them, particularly preferred are a phosphonic acid group and a silyl group (a trialkoxysilyl group, or a trihydroxysilyl group), as they have high bonding force to an electroconductive or semiconductive nano structure.

Among electrochromic compounds represented by the general formula (I), the more preferable embodiment thereof is an electrochromic compound represented by the following general formula (IV):

General Formula (IV)

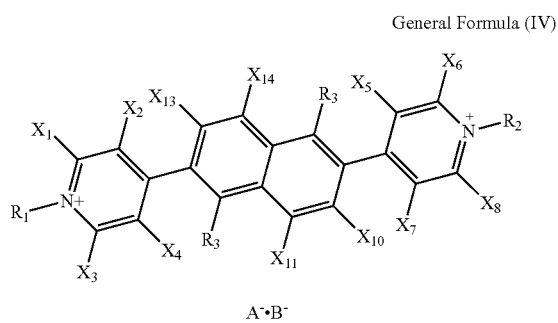

A⁻·B⁻

In the general formula (IV), $X_1$, $X_2$, $X_3$, $X_4$, $X_5$, $X_6$, $X_7$, $X_8$, $X_{10}$, $X_{11}$, $X_{13}$ and $X_{14}$ are each independently a hydrogen atom or a monovalent substituent; $R_3$ is a substituted or unsubstituted alkyl group, or a substituted or unsubstituted alkoxy group; $R_1$ and $R_2$ are each independently a monovalent substituent; and $A^-$ and $B^-$ are each independently a monovalent anion.

In the general formulae (I) and (IV), $A^-$ and $B^-$ are each a monovalent anion, which may be the same or different. The monovalent anions represented by $A^-$ and $B^-$ are not particularly limited, as long as they are monovalent anions that stably pair with cation sites. Preferable examples thereof include Br ion ($Br^-$), Cl ion ($Cl^-$), $ClO_4$ ion ($ClO_4^-$), $PF_6$ ion ($PF_6^-$), and $BF_4$ ion ($BF_4^-$).

Note that, the electrochromic compound of the present invention preferably has X (e.g., $X_1$, $X_2$, $X_3$, $X_4$, $X_5$, $X_6$, $X_7$, and $X_8$) and R (e.g., $R_1$, and $R_2$) which makes the general formula (I) a symmetrical structure, in view of easiness of synthesis thereof, and improvement of stability thereof. Moreover, the electrochromic compound of the present invention colors in cyan, but can color in magenta or yellow due to the aforementioned effect of substituents.

Specific examples of the electrochromic compound of the present invention are presented below, but the electrochromic compound of the present invention is not limited to these examples. Note that, in the following specific examples, Y in the general formula (I) may be the general formula (II) or the general formula (III).

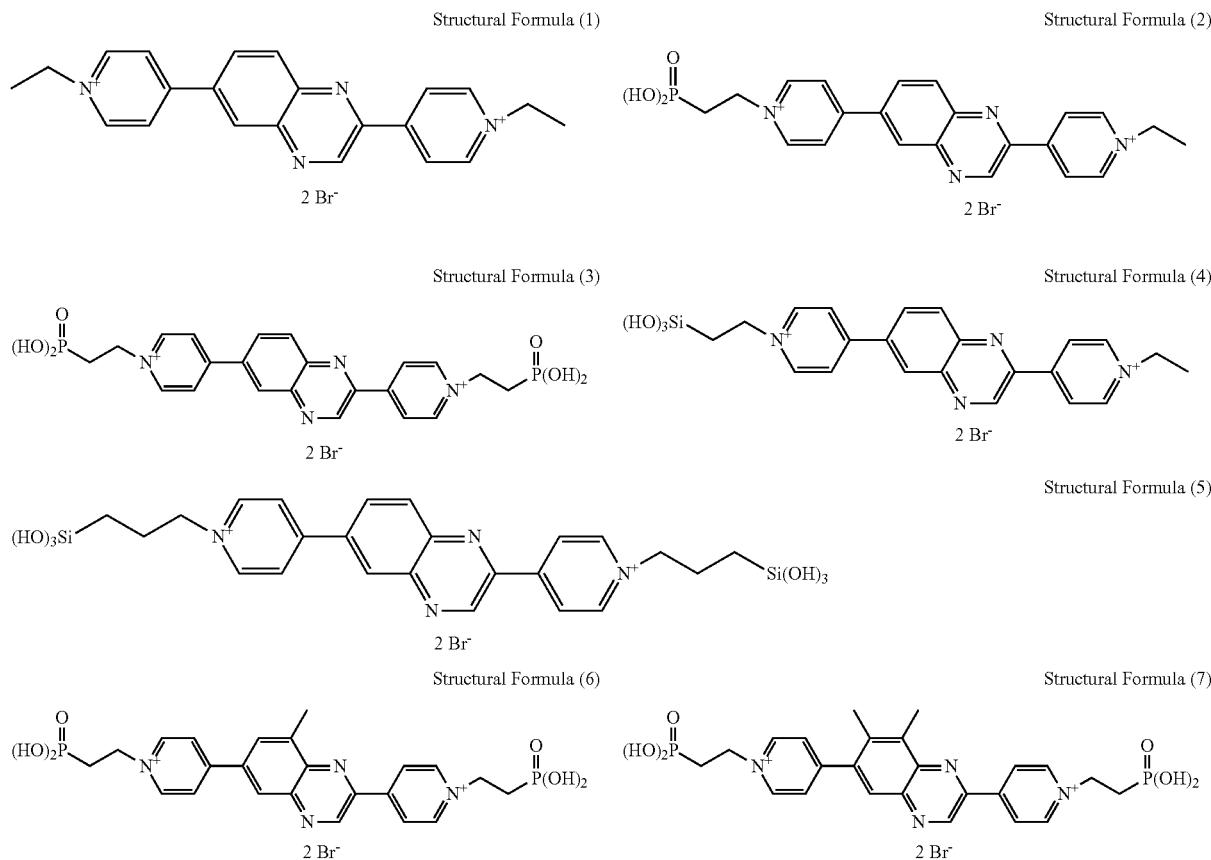

Structural Formula (8)

Structural Formula (9)

Structural Formula (10)

Structural Formula (11)

Structural Formula (12)

Structural Formula (13)

Structural Formula (14)

Structural Formula (15)

Structural Formula (16)

Structural Formula (17)

Structural Formula (18)

Structural Formula (19)

Structural Formula (20)

Structural Formula (21)

-continued
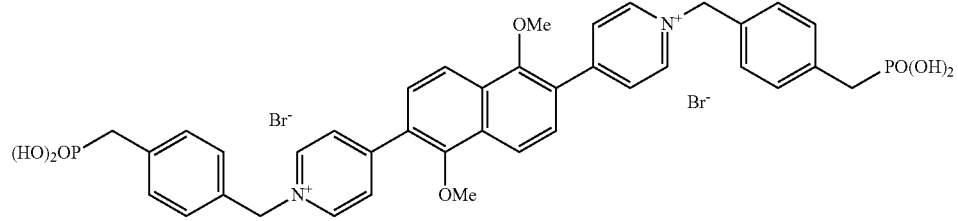
Structural Formula (22)
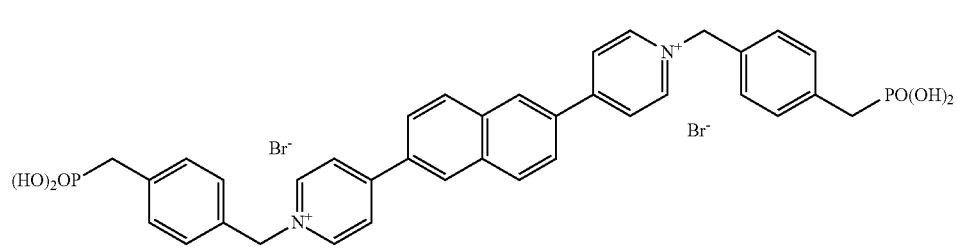
Structural Formula (23)
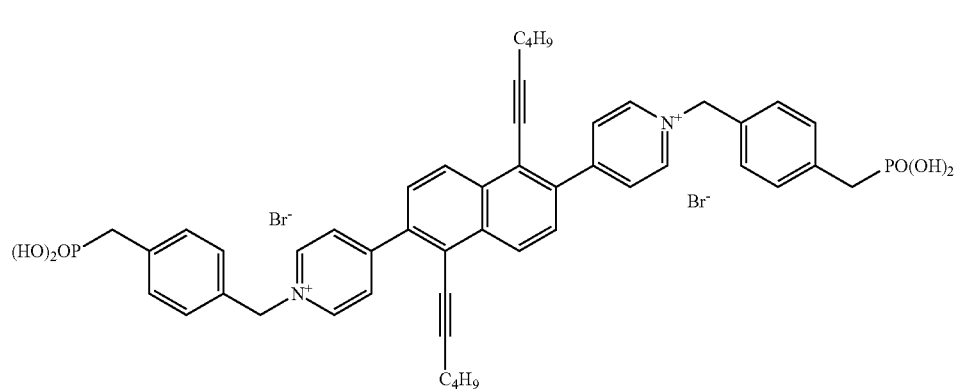
Structural Formula (24)
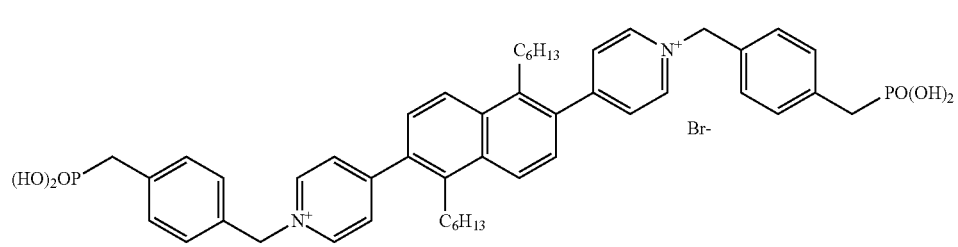
Structural Formula (25)
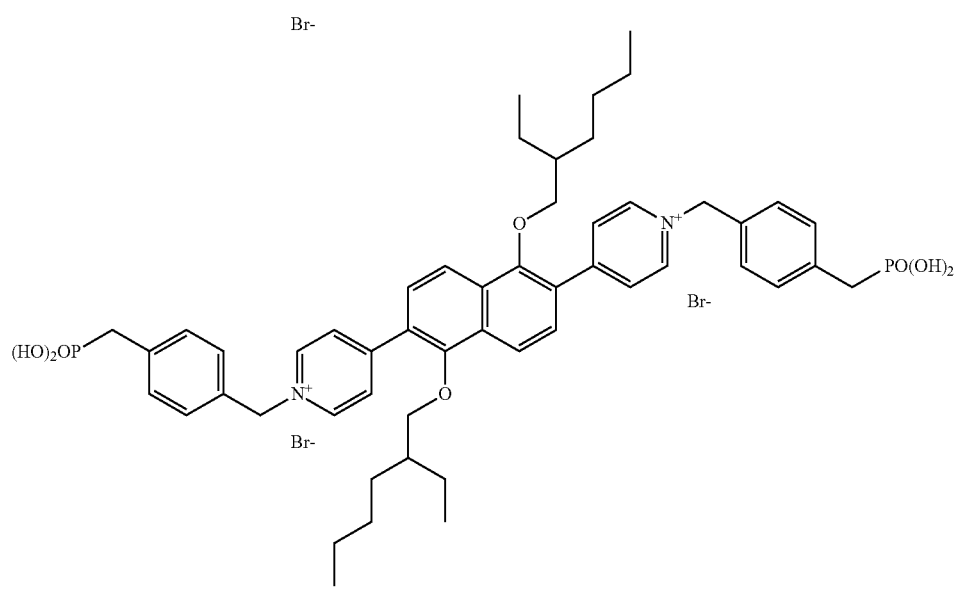
Structural Formula (26)

Structural Formula (27)

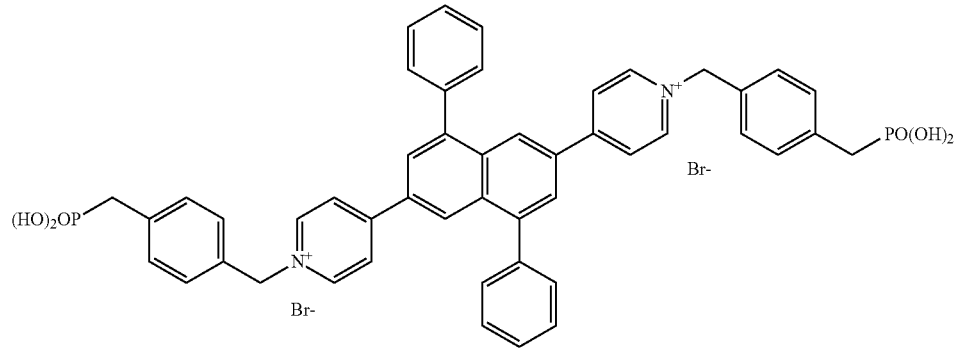

Structural Formula (28)

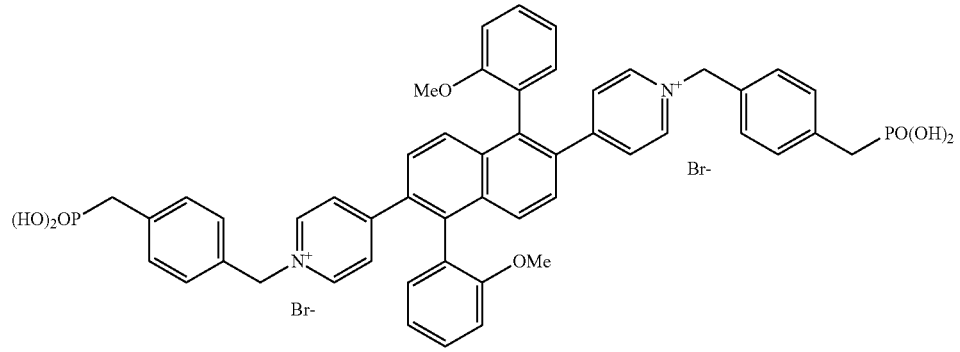

Structural Formula (29)

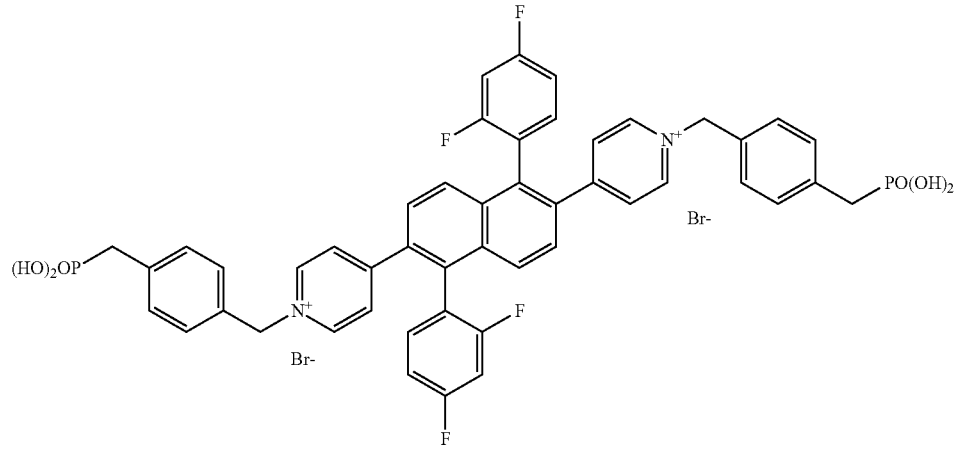

Structural Formula (30)

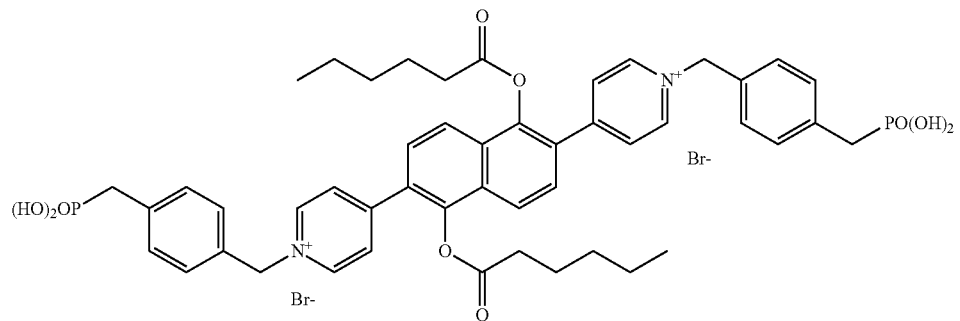

Electrochromic Composition

The electrochromic composition of the present invention contains an electroconductive or semiconductive nano structure, and the electrochromic compound (the electrochromic compound represented by the general formula (I)) of the present invention bonded to or adsorbed onto the nano structure, and may further contain other components, if necessary.

In the electrochromic composition of the present invention, the electrochromic compound is bonded to the electroconductive or semiconductive nano structure.

When the electrochromic composition of the present invention is used in an electrochromic display element, the resulting electrochromic display element colors in cyan, and has excellent memory of an image, i.e., color image retentiveness. Note that, the electroconductive or semiconductive nano structure is nano particles, or a nano-order structure having surface irregularities, such as a nano porous structure.

In the case where either $R_1$ or $R_2$ or both thereof has a functional group capable of directly or indirectly bonding to a hydroxyl group as mentioned above, for example, in the case where the electrochromic compound of the present invention contains a sulfonic acid group, a phosphoric acid group, or a carboxyl group as a binding or adsorbing structure, the electrochromic compound easily forms a complex with the nano structure to thereby form an electrochromic composition having excellent color image retantiveness. A plurality of the aforementioned sulfonic acid group(s), phosphoric acid group(s), and/or carboxyl group(s) may be contained in the electrochromic compound. In the case where the electrochromic compound of the present invention contains a silyl group or a silanol group, moreover, the electrochromic compound bonds to the nano structure through a siloxane bond, which forms a strong bond between the electrochromic compound and the nano structure, to thereby provide a stable electrochromic composition. The siloxane bond described herein means a chemical bond via a silicon atom and an oxygen atom. Moreover, the bonding method, embodiments, and the like of the electrochromic composition are not particularly limited, provided that the electrochromic composition has a structure where the electrochromic compound and the nano structure are bonded with a siloxane bond.

A material for constituting the electroconductive or semiconductive nano structure is preferably metal oxide in view of its transparency and electroconductivity. Examples of the metal oxide include metal oxides containing, as a main component, titanium oxide, zinc oxide, tin oxide, aluminum oxide (abbrev., alumina), zirconium oxide, cerium oxide, silicon oxide (abbrev., silica), yttrium oxide, boron oxide, magnesium oxide, strontium titanate, potassium titanate, barium titanate, calcium titanate, calcium oxide, ferrite, hafnium oxide, tungsten oxide, iron oxide, copper oxide, nickel oxide, cobalt oxide, barium oxide, strontium oxide, vanadium oxide, aluminosilicate, calcium phosphate, or aminosilicate. These metal oxides may be used alone, or in combination as a mixture.

Considering electric properties, such as electric conductivity, and physical properties, such as optical properties, it is possible to display in multicolor with excellent coloring-bleaching response speed when at least one metal oxide selected from the group consisting of titanium oxide, zinc oxide, tin oxide, alumina, zirconium oxide, iron oxide, magnesium oxide, indium oxide, and tungsten oxide is used. Especially when titanium oxide is used, multicolor display having even more excellent coloring-bleaching response speed is possible.

As for the shape of the metal oxide, preferred are metal oxide particles having the average primary particle diameter of 30 nm or smaller. Use of the smaller particle diameter thereof improves transmittance of light to the metal oxide, and realizes use of a shape having a large surface area per unit (referred to as "specific surface area" hereinafter). Use of the metal oxide having a large specific surface area can more efficiently bear the electrochromic compound thereon, which realizes multicolor display having excellent display contrast of coloring and bleaching. The specific surface area of the nano structure is not particularly limited, but, for example, the specific surface area thereof is designed to be 100 m$^2$/g or greater.

Display Element

The display element of the present invention contains a display electrode, a counter electrode provided to face the display electrode and to be spaced from the display element, an electrolyte provided between the display electrode and the counter electrode, and a display layer provided on a surface of the display electrode at the side of the counter electrode where the display layer contains an electrochromic compound represented by the general formula (I), and may further contain other members, if necessary.

Figure 1B:
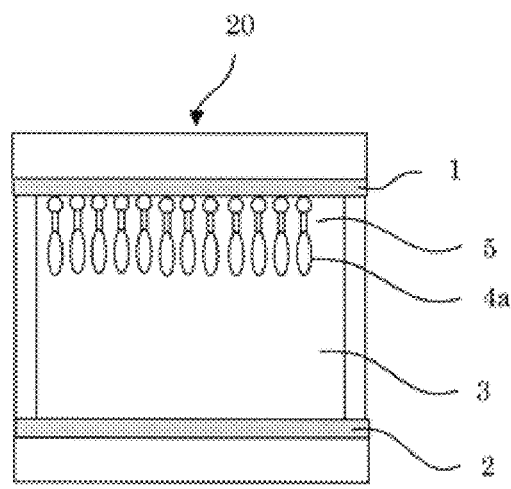
FIG. 1B is a schematic diagram illustrating a structural example of a typical display element using the electrochromic compound of the present invention.

Structural examples of a typical display element using the electrochromic compound of the present invention are depicted in FIGS. 1A and 1B. As illustrated in FIGS. 1A and 1B, the display element 10, 20 of the present invention contains a display electrode 1, and a counter electrode 2 provided to fact the display electrode 1 and to be spaced from the display electrode 1, and an electrolyte 3 provided between the both electrodes (the display electrode 1 and the counter electrode 2), and the display element 10, 20 has a display layer 5 containing at least the electrochromic compound 4a of the present invention on a surface of the display electrode 1 at the counter electrode 2 side (the side facing the counter electrode 2) thereof.

Figure 2:
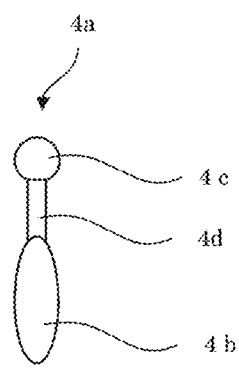
FIG. 2 is a schematic diagram illustrating a structural example of the electrochromic compound of the present invention.

In the display element of 1B, the display layer 5 is formed on a surface of the display electrode 1 at the counter electrode 2 side thereof using the electrochromic compound 4a of the present invention. As for the forming method, any of methods, such as immersing, dipping, vapor deposition, spin coating, printing, and inkjet printing, may be used. In the case where the molecular structure of the electrochromic compound 4a of the present invention contains an adsorbing group (bonding group) 4c, as illustrated in FIG. 2, the adsorbing group 4c is adsorbed on the display electrode 1 to form the display layer 5. In this case, as illustrated in FIG. 2, oxidation-reduction coloring section 4b, which colors, is linked with the adsorbing group 4c via the spacer section 4d, which constitutes the electrochromic compound 4a.

As illustrated in 1A, moreover, it is also possible that a solution is formed by dissolving an electrolyte in a solvent, and the electrochromic compound 4a is dissolved in the solution. In this case, the electrochromic compound 4a is colored and bleached by an oxidation-reduction reaction only at a surface of the electrode. Specifically, within the solution containing the electrochromic compound, the surface of the display electrode 1 facing the counter electrode 2 functions as a display layer.

Figure 3:
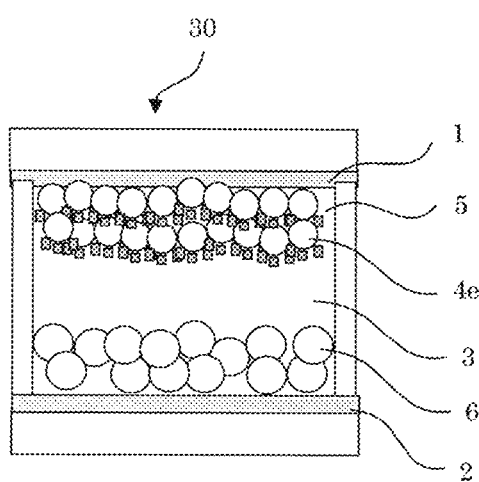
FIG. 3 is a schematic diagram illustrating another structural example of a typical display element using the electrochromic composition of the present invention.

Another structural example of a typical display element using the electrochromic compound of the present invention is depicted in FIG. 3.

The display element 30 of the present invention contains a display electrode 1, a counter electrode 2 provided to face the display electrode 1 and to be spaced from the display electrode 1, an electrolyte 3 provided between the both electrodes (the display electrode 1 and the counter electrode 2), and a display layer 5 containing at least the electrochromic composite 4e of the present invention, which is provided on a surface of the display electrode 1 at the side of the counter electrode 2. Moreover, the display element 30 contains a white reflecting layer 6 formed of white particles provided on a surface of the counter electrode 2 at the side of the display electrode 1 (the surface thereof facing the display electrode 1).

In the display element illustrated in FIG. 3, the display layer 5 is formed on a surface of the display electrode 1 at the side of the counter electrode 2 using the electrochromic composition 4e of the present invention. As for the forming method, any of methods, such as immersing, dipping, vapor deposition, spin coating, printing, and inkjet printing, may be used. As illustrated in FIG. 2, the molecular structure of the electrochromic compound 4a in the electrochromic composition 4e of the present invention contains a bonding group 4c, and the bonding group 4c is bonded to the electroconductive or semiconductive nano structure to constitute the electrochromic composition 4e. The electrochromic composition 4e is provided as a layer on the display electrode 1, to thereby form the display layer 5.

The electrochromic compound in the electrochromic composition of the present invention can contain, in the molecular structure thereof, a functional group capable of directly or indirectly bonding to a hydroxyl group (adsorbing group), so-called a bonding group, and therefore the bonding group is bonded to the electroconductive or semiconductive nano structure to constitute the electrochromic composition. The electrochromic composition is provided as a layer on the display electrode 1 to thereby form the display layer 5.

Materials used for constituting the electrochromic display elements 10, 20, and 30 according to the embodiments of the present invention are explained hereinafter.

As for a material for constituting the display electrode 1, a transparent electric conductive substrate is desirably used. As for the transparent electric conductive substrate, preferred is a substrate, in which a transparent electric conductive film is coated on glass or a plastic film. In the case of the plastic film, a light and flexible display element can be produced.

A material of the transparent electric conductive film is not particularly limited as long as it is a material having electric conductivity. However, it is necessary to secure transmittance of light. Therefore, use of a transparent electric conductive material, which is transparent and has excellent electric conductivity, is desirable. Use of such material can enhance the visibility of a color to be colored.

As for the transparent electric conductive material, an inorganic material, such as tin-doped indium oxide (abbrev.: ITO), fluorine-doped tin oxide (abbrev.: FTO), and antimony-doped tin oxide (abbrev.: ATO), can be used, but the transparent electric conductive material is particularly preferable an inorganic material containing indium oxide (referred to as "In oxide" hereinafter), tin oxide (referred to as "Sn oxide" hereinafter), or zinc oxide (referred to as "Zn oxide" hereinafter). The In oxide, Sn oxide, and Zn oxide are materials that can be easily formed into a film by sputtering, and also are materials that can attain both excellent transparency and electric conductivity. Moreover, the particularly preferable materials are InSnO, GaZnO, SnO, $In_2O_3$, and ZnO.

Examples of a material for constituting a display substrate (reference number is not depicted), on which the display electrode 1 is provided, include glass, and plastic. When a plastic film is used as the display substrate, a light and flexible display element can be produced.

As for the counter electrode 2, a transparent electric conductive film formed of ITO, FTO, or zinc oxide, an electric conductive metal film formed of zinc or platinum, or carbon may be used. The counter electrode 2 is also typically formed on a counter substrate (reference number is not depicted). The counter electrode substrate is also preferably glass, or a plastic film. In the case where a metal plate, such as zinc, is used as the counter electrode 2, the counter electrode 2 also functions as a substrate.

In the case where a material for constituting the counter electrode 2 is a material that induces a reverse reaction, which is reverse to the oxidization-reduction reaction induced by the electrochromic composition of the display layer, stable coloring and bleaching are possible. Specifically, when a material, which induces a reduction reaction in the case where the electrochromic composition is colored by oxidization, or induces an oxidization reaction in the case where the electrochromic composition is colored by reduction, is used as the counter electrode 2, reactions of coloring and bleaching in the display layer 5 containing the electrochromic composition become more stable.

As for a material for constituting the electrolyte 3, a solution in which a supporting electrolyte is dissolved in a solvent is typically used.

Examples of the supporting electrolyte include: an inorganic ionic salt, such as alkali metal salt, and alkali earth metal salt; quaternary ammonium salt; acid; and alkali. Specific examples thereof include $LiClO_4$, $LiBF_4$, $LiAsF_6$, $LiPF_6$, $CF_3SO_3Li$, $CF_3COOLi$, KCl, $NaClO_3$, NaCl, $NaBF_4$, NaSCN, $KBF_4$, $Mg(ClO_4)_2$, and $Mg(BF_4)_2$.

Moreover, examples of the usable solvent include propylene carbonate, acetonitrile, γ-butyrolactone, ethylene carbonate, sulfolane, dioxolane, tetrahydrofuran, 2-methyltetrahydrofuran, dimethylsulfoxide, 1,2-dimethoxyethane, 1,2-ethoxymethoxyethane, polyethylene glycol, and alcohol.

As the electrolyte is not particularly limited to a fluid electrolyte in which a supporting electrolyte is dissolved in a solvent, other than the examples mentioned above, a gel electrolyte, or a solid electrolyte, such as a polymer electrolyte can also be used. Examples of the solid electrolyte include a perfluorosulfonic acid-based polymer membrane. The solution electrolyte has an advantage that it has high ion conductivity, and the solid electrolyte is suitable for producing an element that does not deteriorate and has high durability.

In the case where the display element of the present invention is used as a reflecting display element, moreover, it is preferred that a white reflecting layer 6 be provided between the display electrode 1 and counter electrode 2, as illustrated in FIG. 3. As for the formation of the white reflecting layer 6, the simplest production method thereof is dispersing white pigment particles in a resin, and applying the resultant onto the counter electrode 2.

As for the white pigment particles, particles formed of typical metal oxide can be used. Specific examples thereof include titanium oxide, aluminum oxide, zinc oxide, silicon oxide, cesium oxide, and yttrium oxide. Moreover, the electrolyte can be also functioned as a white reflecting layer by mixing the white pigment particles in a polymer electrolyte.

As for a driving method of the display elements 10, 20, and 30, any method may be used as long as the predetermined voltage and current can be applied. Use of a passive driving system can produce an inexpensive display element. Moreover, use of an active driving system can perform display of high definition and high speed. The active driving can be easily realized by providing active driving elements on the counter substrate.

EXAMPLES

The electrochromic compound and electrochromic composition of the present invention, and a display element using the electrochromic compound and electrochromic composition are explained through Examples, but these Examples shall not be construed as to limit the scope of the present invention.

Example 1

Synthesis of Electrochromic Compound [Structural Formula (21)]

According the following synthesis flows (a) and (b), the electrochromic compound represented by the structural formula (21) was synthesized.

<a> Synthesis of Intermediate Product (21-1)

Synthesis Flow (a)

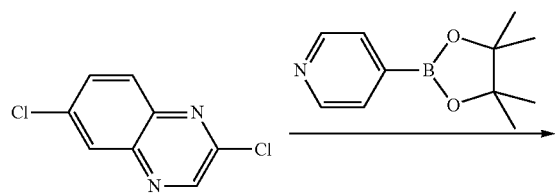

Intermediate Product (21-1)

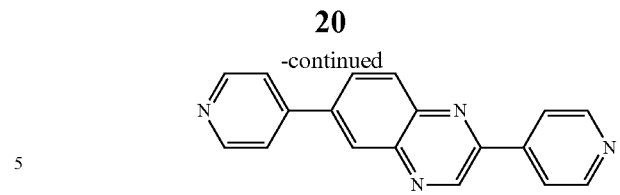

A 100 mL three-necked flask was charged with 0.594 g (3.00 mmol) of 2,6-dichloroquinoxaline, 1.72 g (8.4 mmol) of 4-(4,4,5,5-tetramethyl-1,3,2-dioxaborolan-2-yl)pyridine, 0.055 g (0.060 mmol) of tris(dibenzylideneacetone)dipalladium(0), and 0.053 g (0.144 mmol) of triicyclohexylphosphonium tetrafluoroborate, and was purged with argon gas. Thereafter, to the flask, 11 mL of 1,4-dioxane and 8 mL of a 1.27M-tripotassium phosphate aqueous solution, which had been degassed with argon gas, were added in this order, and the resultant was subjected to reflux for 4 hours at 100° C. Thereafter, the reaction solution was cooled to room temperature, and chloroform and a saturated salt solution were added to the reaction solution. The resulting solution was transferred into a separating funnel, and the organic layer was washed with a saturated salt solution. Thereafter, magnesium sulfate serving as a drying agent was added to the organic layer, and the mixture was stirred for 1 hour to remove water. Subsequently, 1 g of palladium scavenger silica gel (manufactured by Sigma-Aldrich Japan) was added, and the resultant was stirred for 1 hour at room temperature, to remove the palladium remained in the organic layer. After separating the drying agent and the silica gel through filtration, the solvent was removed under the reduced pressure. The resulting crude product was purified by silica-gel column chromatography (toluene/acetone=½), to thereby obtain a target product (yielded amount: 0.638 g, yield: 75%).

<b> Synthesis of Electrochromic Compound [Structural Formula (21)]

Synthesis Flow (b)

Structural Formula (21)

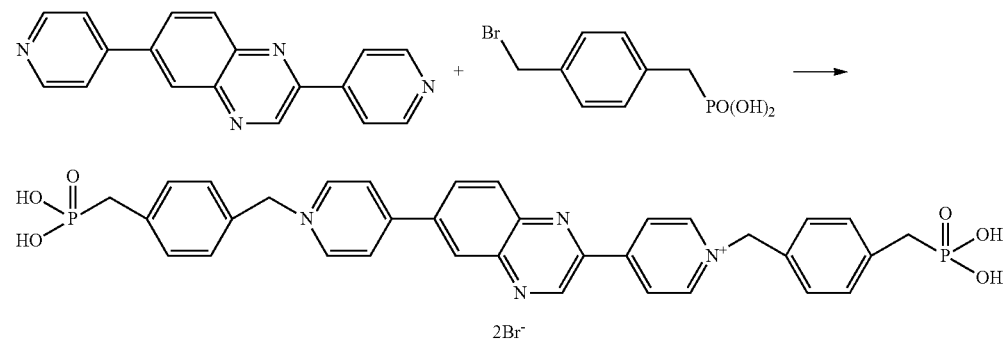

A 25 mL three-necked flask was charged with 0.114 g (0.40 mmol) of 2,6-bis(4-pyridyl)-quinoxaline, 0.358 g (1.35 mmol) of 4-bromomethylbenzylphosphonic acid, and 3.0 mL of dimethylformamide, and the resulting mixture was allowed to react for 2 hours at 90° C. After cooling the reaction solution to room temperature, the solution was released into 2-propanol. Subsequently, the obtained solids were dispersed in 2-propanol, followed by collecting the solids. Then, the solids were dried for 2 days at 100° C. under reduced pressure, to thereby obtain a target product (yielded amount: 0.272 g, yield: 85%).

Production and Evaluation of Electrochromic Display Element (a) Formation of Display Electrode and Electrochromic Display Layer First, a glass substrate with FTO electric conductive film in the size of 25 mm×30 mm (manufactured by AGC Fabritech Co., Ltd.) was provided. Onto the 19 mm×15 mm region of the top surface of the glass substrate, a titanium oxide nano particle dispersion liquid (SP210, manufactured by Showa Titanium K.K.) was applied by spin coating, followed by performing annealing for 15 minutes at 120° C., to thereby form a titanium oxide particle film. Onto the titanium oxide particle film, a 1% by mass 2,2,3,3-tetrafluoropropanol solution of the compound represented by the structural formula (21) was applied by spin coating, and the applied solution was subjected to annealing for 10 minutes at 120° C., to thereby form a display layer 5 having an electrochromic composition, in which the electrochromic compound had been adsorbed on the surfaces of the titanium oxide particles.

(b) Formation of Counter Electrode

Separately from the glass substrate, a glass substrate with an ITO electric conductive film (manufactured by GEOMATEC Co., Ltd.) in the size of 25 mm×30 mm was prepared and provided as a counter substrate.

(c) Production of Electrochromic Display Element

A cell was produced by bonding the display substrate and the counter substrate together via a spacer having a thickness of 75 μm.

Next, titanium oxide particles (CR50, manufactured by ISHIHARA SANGYO KAISHA, LTD.) having the primary particle diameter of 300 nm were dispersed, in an amount of 35% by mass, in a solution, in which 20% by mass of tetrabutylammonium perchlorate had been dissolved in dimethyl sulfoxide, to thereby prepare an electrolyte solution. The electrolyte solution was then enclosed in the cell, to thereby produce an electrochromic display element. The structure of electrochromic display element is presented in FIG. 3.

Coloring/Bleaching Test

Figure 4:
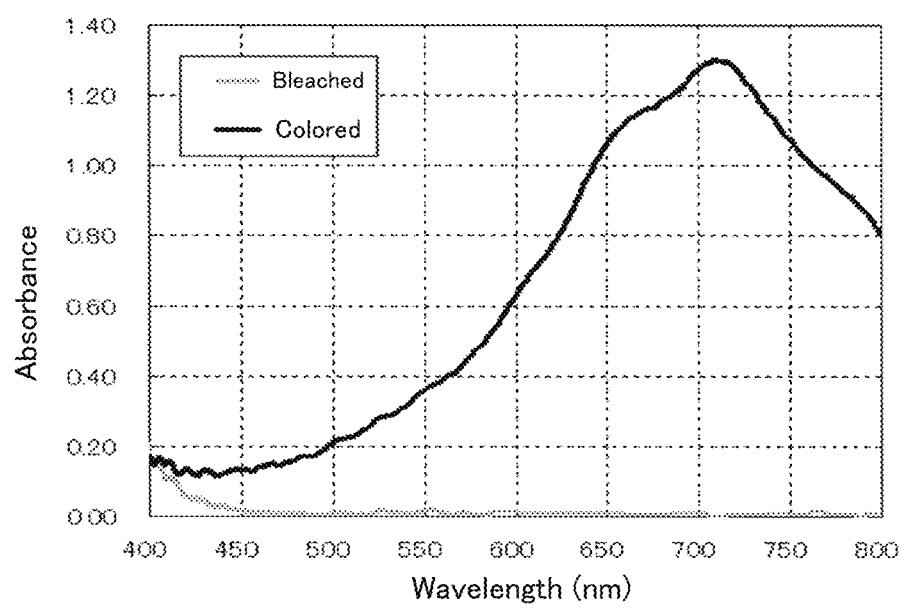
FIG. 4 is a diagram depicting absorption spectrums of the display electrode of Example 1, on which the electrochromic display layer is formed, in the bleached state and the colored state.

The electrochromic display layer formed in Example 1 was placed in a quartz cell. As for a counter electrode, a platinum electrode was used. As for a reference electrode, an Ag/Ag$^+$ electrode (RE-7, manufactured by BAS Inc.) was used. The cell was filled with an electrolytic solution prepared by dissolving 0.1 M of tetrabutylammonium perchlorate in dimethyl sulfoxide. To this quartz cell, light was applied from a deuterium tungsten halogen light source (DH-2000, manufactured by Ocean Optics, Inc.). The transmitted light was detected by a spectrometer (USB4000, manufactured by Ocean Optics, Inc.), to measure the absorption spectrum. The absorption spectrums of the bleached state and colored state are presented in FIG. 4. In the bleached state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the maximum absorption wavelength was 710 nm, and the electrochromic display layer colored in vivid cyan.

The evolution of coloring/bleaching was performed on the electrochromic display element produced in Example 1. The evaluation of coloring/bleaching was carried out by applying diffused light using a spectrophotometer MCPD7700, manufactured by Otsuka Electronics Co., Ltd.

In the bleached state before applying the voltage, the electrochromic display element of Example 1 had no color, and was white.

When a voltage of 3.0 V was applied to this display electrode for 2 seconds by connecting a negative electrode to the display electrode 1 of the display element and connecting a positive electrode to the counter electrode 2 thereof, the electrochromic display element of Example 1 colored in vivid cyan.

Figure 5:
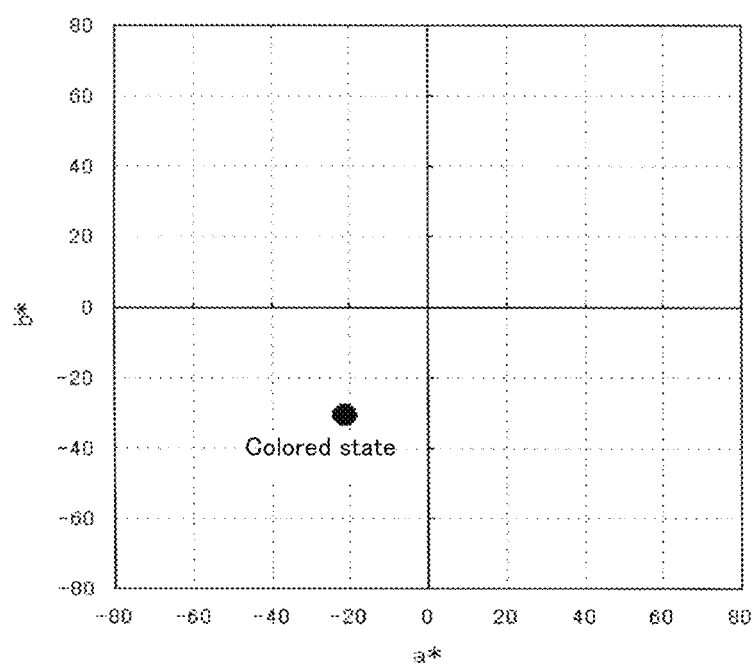
FIG. 5 is a diagram depicting a color value of the electrochromic display element produced in Example 1.

The measured color value is depicted in FIG. 5 using CIE LAB scale.

Example 2

An electrochromic compound [the compound represented by the structural formula (1) listed earlier] was synthesized by allowing the intermediate product 22-1 synthesized in Example 1 to react with 2 equivalents of ethyl bromide.

Next, in 2,2,3,3-tetrafluoropropanol, 1% by mass of the synthesized electrochromic compound [the compound represented by the structural formula (1)] and 5% by mass of tetrabutylammonium perchlorate serving as an electrolyte were dissolved, to thereby prepare an electrochromic compound solution. This electrochromic compound solution was enclosed in a cell prepared by bonding glass substrates each with an ITO electric conductive film in the size of 30 mm×30 mm (manufactured by GEOMATEC Co., Ltd.) together as a display substrate and a counter substrate via a spacer having a thickness of 75 μm, to thereby produce an electrochromic display element. The structure of the electrochromic display element is presented in FIG. 1.

When a voltage of 3 V was applied to the display element produced in Example 2 for 2 seconds, the display element was colored in cyan. When a reverse voltage of −2V was applied to the display element for 1 second, the color was bleached and the display element was returned to transparent. It was confirmed that the electrochromic compound of the present invention colored in cyan as it was colored, and moreover, no color was left as it was bleached.

Example 3

An electrochromic compound (Ex.-3) was synthesized in accordance with the following scheme.

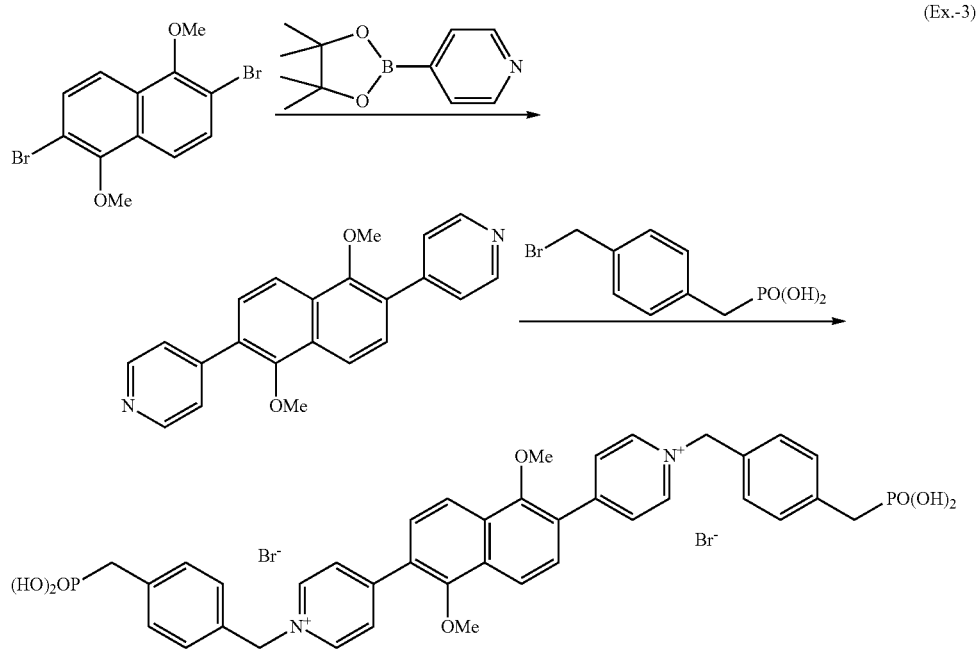

(a) Synthesis of Intermediate Product (1,5-dimethoxy-2,6-di(4-pyridyl)naphthalene)

A 50 mL-flask was charged with 0.658 g (1.90 mmol) of 2,6-dibromo1,5-dimethoxynaphthalene, 1.560 g (7.61 mmol) of 4-(4,4,5,5-tetramethyl1,3,2-dioxaborolan-2-yl)pyridine, 70 mg (0.076 mmol) of tris(dibenzylideneacetone)dipalladium(0), and 67 mg (0.182 mmol) of tricyclohexylphosphine tetrafluoroborate, and then purged with argon. Thereafter, 2.16 g of tripotassium phosphate, 7 mL of water, and 7 mL of 1,4-dioxane were added to the flask, and the resulting mixture was heated and stirred for 18 hours at 95° C. After cooling the reaction solution to room temperature, the precipitated solids were collected through filtration, and then were washed with ethanol and ethyl acetate, to thereby obtain 0.543 g of a target product as colorless crystals.

(b) Synthesis of Electrochromic Compound (Ex.-3)

A 25 mL-flask was charged with 0.539 g (1.57 mmol) of 1,5-dimethoxy-2,6-di(4-pyridyl)naphthalene, 1.460 g (5.51 mmol) of 4-bromomethylbenzylphosphonic acid, and 19 mL of dimethylformamide, and the resulting mixture was stirred for 3 hours at 90° C. After cooling the resulting solution to room temperature, the solution was released into 2-propanol. Subsequently, the obtained solids were collected, to thereby obtain a target product (yielded amount: 1.35 g).

Example 4

An electrochromic compound (Ex.-4) was synthesized in the same manner as in Example 3, provided that 2,6-dibromo1,5-dimethoxynaphthalene was replaced with 2,6-dibromonaphthalene.

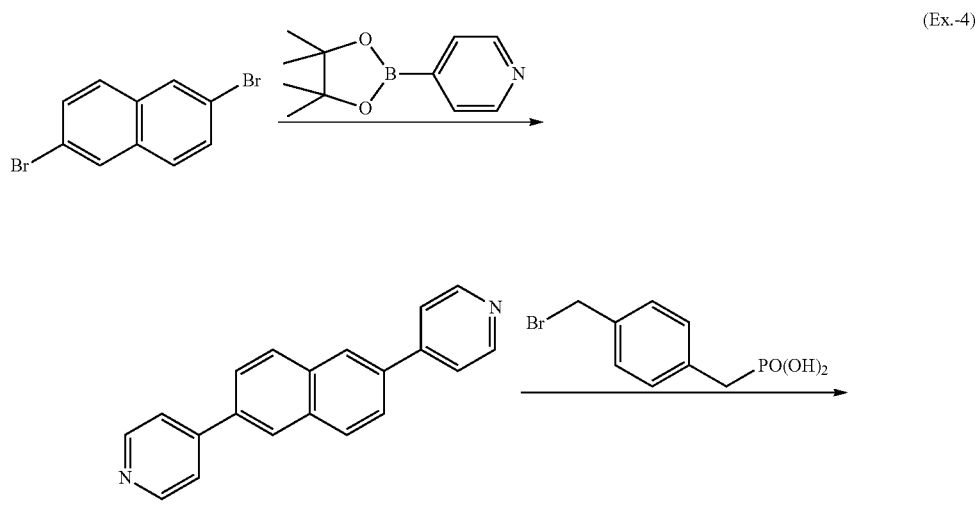

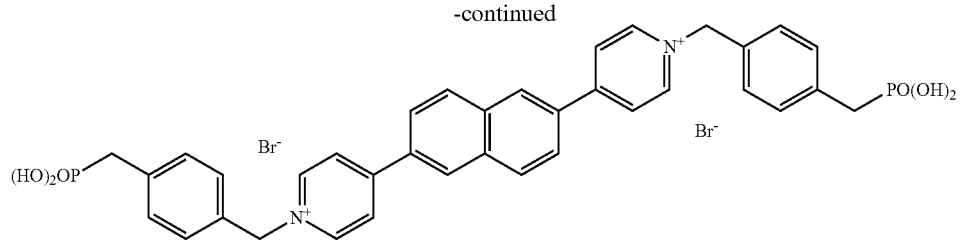
Example 5
An electrochromic compound (Ex.-5) was synthesized in the same manner as in Example 3, provided that 2,6-dibromo-1,5-dimethoxynaphthalene was replaced with 2,6-dibromo1,5-dihexydihexenylnaphthalene.
(Ex.-5)
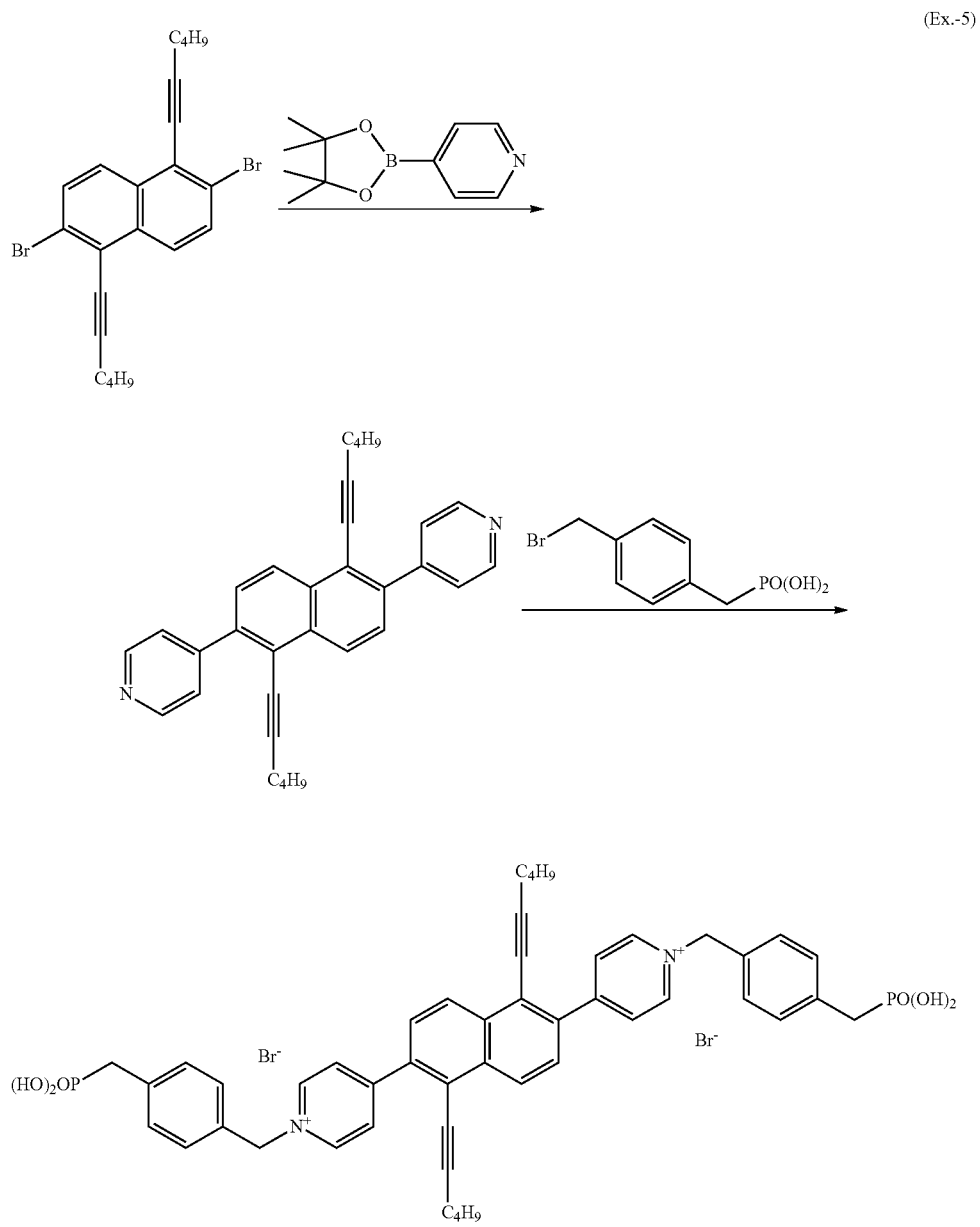

(Example 6) Production of Electrochromic Display Element

(a) Formation of Display Electrode and Electrochromic Display Layer

First, a glass substrate in the size of 30 mm×30 mm was provided. On the 16 mm×23 mm region of the top surface of the glass substrate, an ITO film was formed by sputtering so that a thickness thereof was to be about 100 nm, to thereby form a display electrode 1. A sheet resistance between the terminal edges of the display electrode 1 was measured, and the sheet resistance thereof was about 200Ω.

Next, a titanium oxide nano particle dispersion liquid (SP210, manufactured by Showa Titanium K.K.) was applied onto the glass substrate, on which the display electrode 1 had been formed, by spin coating, and the coating liquid was subjected to annealing for 15 minutes at 120° C., to form a titanium oxide particle film. Subsequently, a 1% by mass 2,2,3,3-tetrafluoroprop anol solution of the electrochromic compound (Ex.-3) synthesized in Example 3 was applied as a coating liquid by spin coating. The coating liquid was subjected to annealing for 10 minutes at 120° C., to thereby form a display layer 5, in which the electrochromic compound was adsorbed on surfaces of the titanium oxide particles.

(b) Formation of Counter Electrode

Separately from the glass substrate above, a glass substrate in the size of 30 mm×30 mm was provided. On the entire top surface of the glass substrate, an ITO film was formed by sputtering so that the thickness thereof to be about 150 nm. Further, on the top surface of the glass substrate on the entire surface of which the transparent electric conductive thin film had been formed, a solution, which had been prepared by adding 25% by mass of 2-ethoxyethyl acetate to a thermocurable electric conductive carbon ink (CH10, manufactured by JUJO CHEMICAL CO., LTD.), was applied by spin coating. The coating solution was subjected to annealing for 15 minutes at 120° C., to thereby form a counter electrode 2.

(c) Production of Electrochromic Display Element

A cell was produced by bonding the display substrate 1 and the counter substrate 2 together via a spacer having a thickness of 75 μm. Next, titanium oxide particles (CR50, manufactured by ISHIHARA SANGYO KAISHA, LTD.) having the primary particle diameter of 300 nm were dispersed, in an amount of 35% by mass, in a solution, in which 20% by mass of tetrabutylammonium perchlorate had been dissolved in dimethyl sulfoxide, to thereby prepare an electrolyte solution. The electrolyte solution was then enclosed in the cell, to thereby produce an electrochromic display element using the electrochromic compound (Ex.-3).

(Example 7) Coloring/Bleaching Test of Produced Electrochromic Display Element A comparative evaluation of coloring and bleaching was performed on the electrochromic display element produced in Example 6. The evaluation of coloring/bleaching was carried out by applying diffused light using a spectrophotometer LCD-5000 manufactured by Otsuka Electronics Co., Ltd.

When a voltage of 3.0 V was applied to this display electrode for 1 second by connecting a negative electrode to the display electrode 1 of the display element and connecting a positive electrode to the counter electrode 2 thereof, the electrochromic display element of Example 6 colored in excellent cyan.

It was confirmed that the electrochromic compound of Example 3 had hardly any color in the bleached state, and exhibited clear cyan color in the colored state.

Moreover, after applying a coloring voltage (3.0 V, 2 seconds), the electrochromic display element produced in Example 6 remained the colored state even 300 seconds later from switching off of the power.

Figure 6:
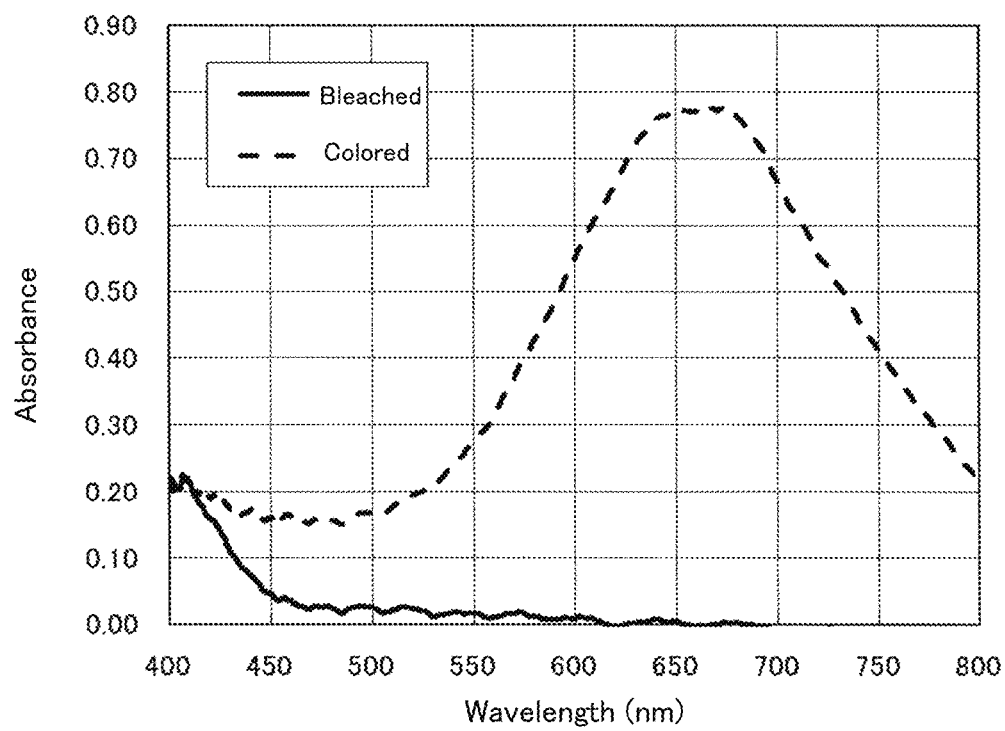
FIG. 6 is a diagram depicting absorption spectrums of the display electrode of Example 3, on which the electrochromic display layer is formed, in the bleached state and the colored state.

The display electrode on which the electrochromic display layer had been formed in Example 6 was placed in a quartz cell. As for a counter electrode, a platinum electrode was used. As for a reference electrode, an Ag/Ag$^+$ electrode (RE-7, manufactured by BAS Inc.) was used. The cell was filled with an electrolytic solution prepared by dissolving tetrabutylammonium perchlorate in dimethyl sulfoxide to give a concentration of 20% by mass. Light was applied to the quartz cell from a deuterium tungsten halogen light source (DH-2000, manufactured by Ocean Optics, Inc.). The transmitted light was detected by a spectrometer (USB4000, manufactured by Ocean Optics, Inc.), to measure the absorption spectrum. The absorption spectrums of the bleached state and colored state are presented in FIG. 6. In the bleached state before applying voltage, there was hardly any absorption in the entire visible region of 400 nm to 800 nm, and the electrochromic display layer was transparent. When the voltage of −1.5 V was applied using a potentiostat (ALS-660C, manufactured by BAS Inc.), the maximum absorption wavelength was around 650 nm, and the electrochromic display layer colored in vivid cyan.

Example 8

Figure 7:
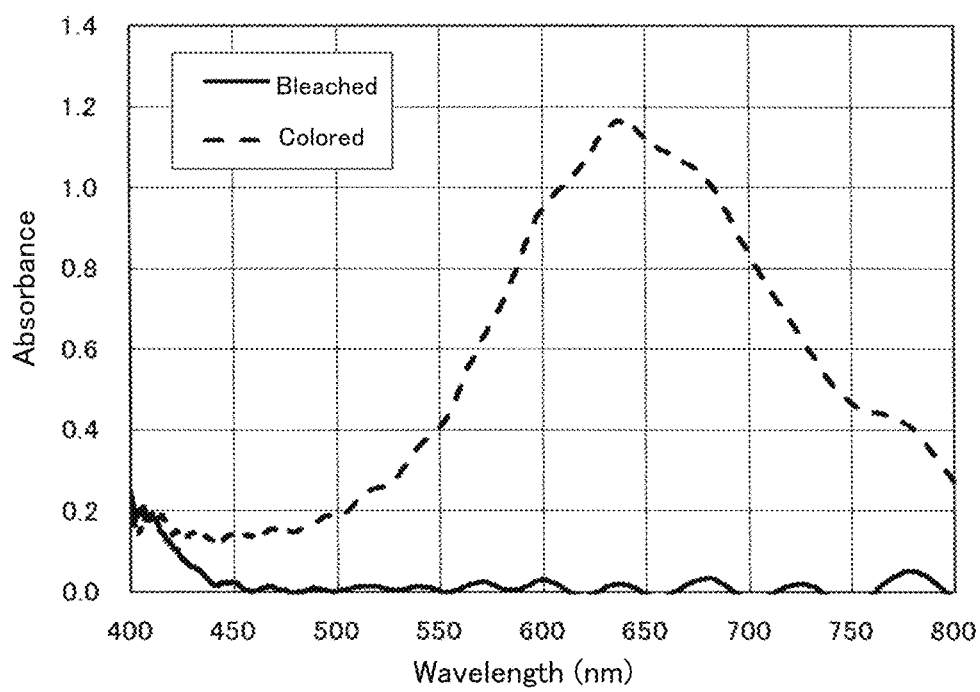
FIG. 7 is a diagram depicting absorption spectrums of the display electrode of Example 4, on which the electrochromic display layer is formed, in the bleached state and the colored state.
Figure 8:
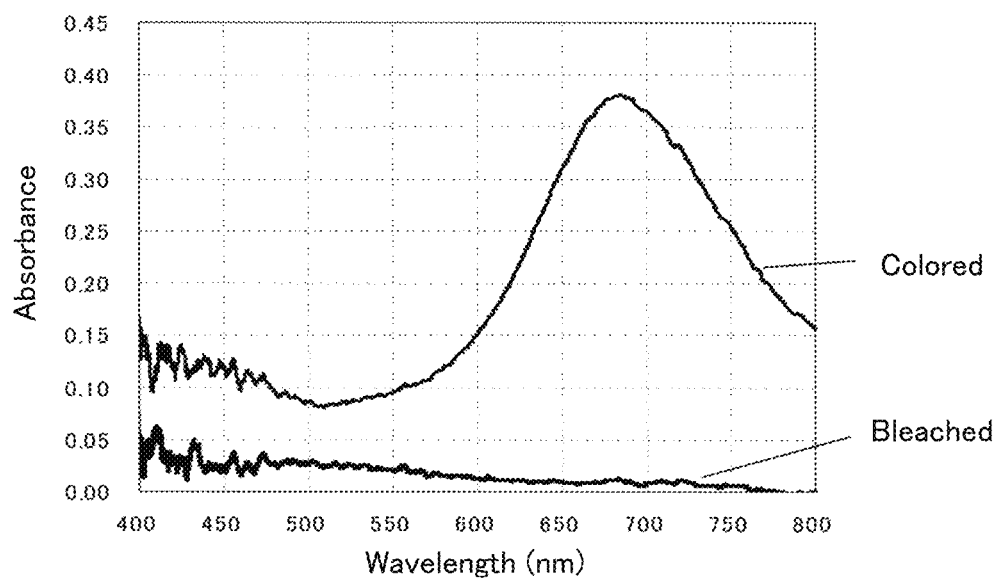
FIG. 8 is a diagram depicting absorption spectrums of the display electrode of Example 10, on which the electrochromic display layer is formed, in the bleached state and the colored state.
Figure 9:
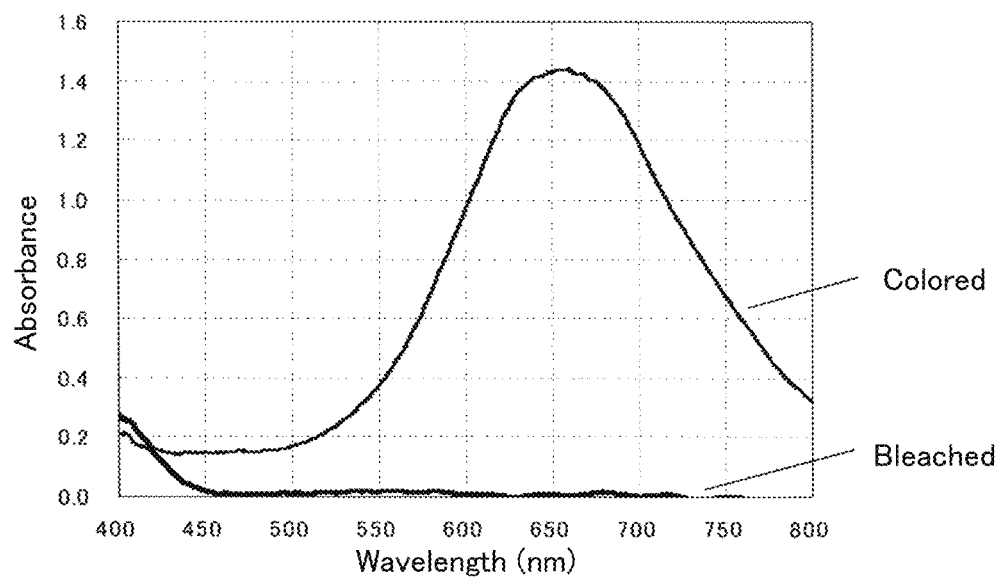
FIG. 9 is a diagram depicting absorption spectrums of the display electrode of Example 11, on which the electrochromic display layer is formed, in the bleached state and the colored state.
Figure 10:
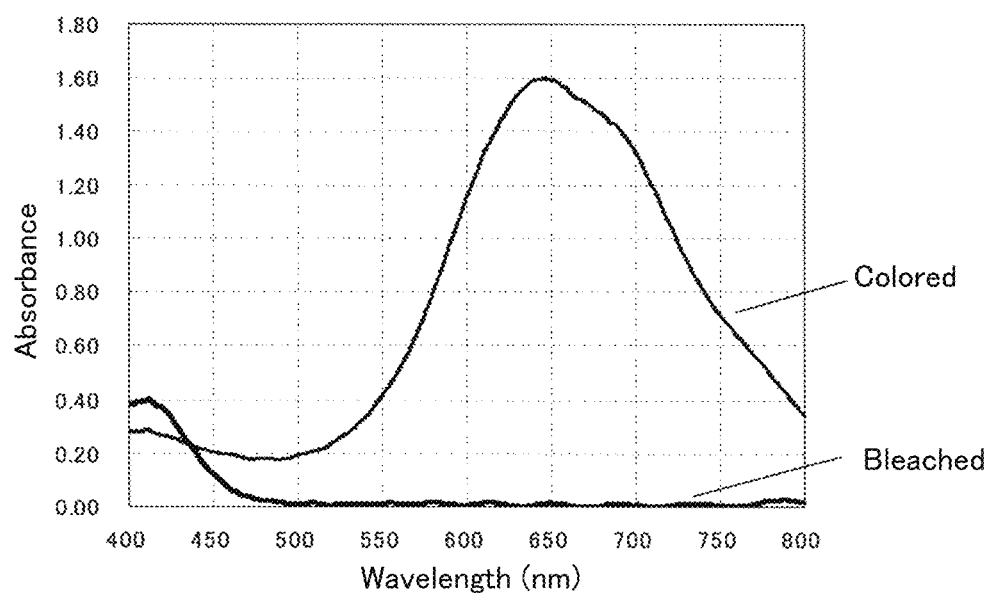
FIG. 10 is a diagram depicting absorption spectrums of the display electrode of Example 12, on which the electrochromic display layer is formed, in the bleached state and the colored state.
Figure 11:
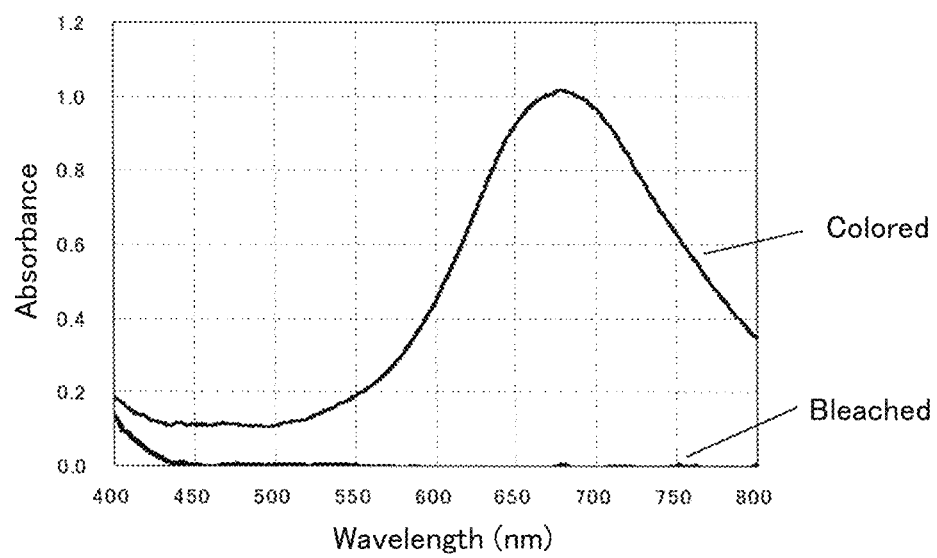
FIG. 11 is a diagram depicting absorption spectrums of the display electrode of Example 13, on which the electrochromic display layer is formed, in the bleached state and the colored state.
Figure 12:
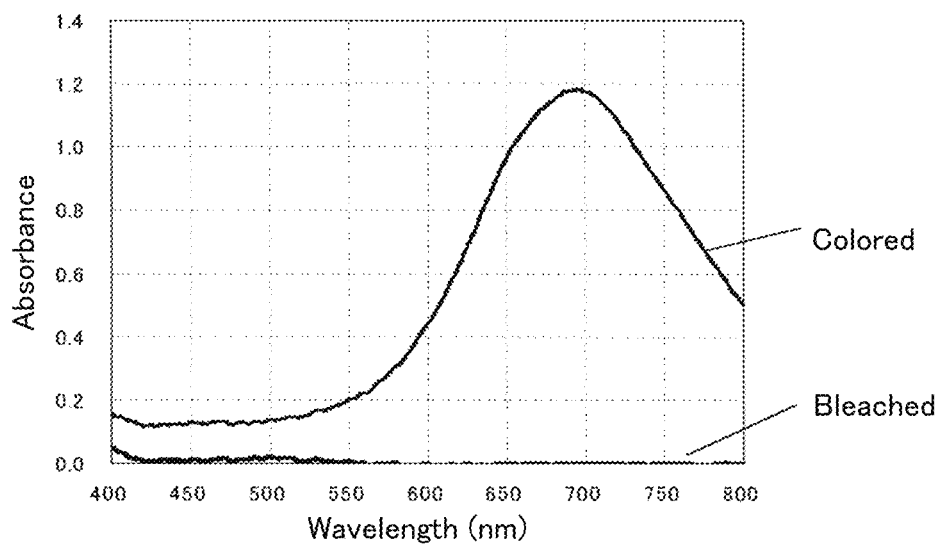
FIG. 12 is a diagram depicting absorption spectrums of the display electrode of Example 14, on which the electrochromic display layer is formed, in the bleached state and the colored state.
Figure 13:
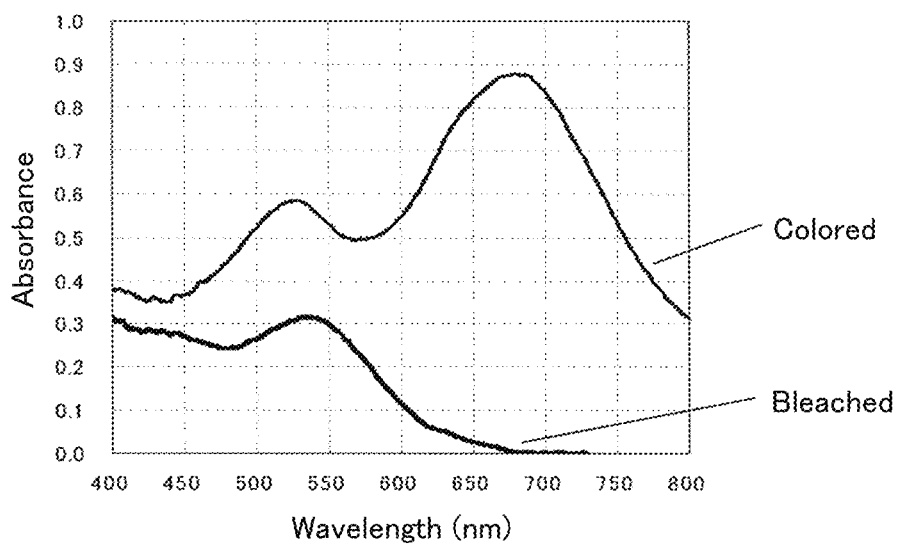
FIG. 13 is a diagram depicting absorption spectrums of the display electrode of Example 15, on which the electrochromic display layer is formed, in the bleached state and the colored state.

An electrochromic display element was produced in the same manner as in Example 6, provided that the compound (Ex.-3) was replaced with the compound (Ex.-4), and absorption spectrums was measured using a quartz cell in the same manner as in Example 6. The absorption spectrums thereof are presented in FIG. 7. Similarly to the compound (Ex.-3), in the bleached state before applying voltage, there was hardly any absorption in the entire visible region of 400 nm to 800 nm, and the electrochromic display layer was transparent. When the voltage of −1.5 V was applied using a potentiostat (ALS-660C, manufactured by BAS Inc.), the maximum absorption wavelength was around 650 nm, and the electrochromic display layer colored in vivid cyan.

Example 9

An electrochromic display element was produced in the same manner as in Example 6, provided that the compound (Ex.-3) was replaced with the compound (Ex.-5), and absorption spectrums was measured using a quartz cell in the same manner as in Example 6. Similarly, in the bleached state before applying voltage, there was hardly any absorption in the entire visible region of 400 nm to 800 nm, and the electrochromic display layer was transparent. When the voltage of −1.5 V was applied using a potentiostat (ALS-660C, manufactured by BAS Inc.), though it was not depicted in the figured, the maximum absorption wavelength was around 725 nm, and the electrochromic display layer colored in cyan.

Example 10

Using 0.02 g of 1,5-dihexynyl-2,6-di(4-pyridyl)naphthalene, which was the synthesis intermediate product of the electrochromic compound (Ex.-5), 0.04 g of 5% Pd/C (palladium carbon), and 100 mL of toluene, hydrogenation was performed under a flow of hydrogen gas. The obtained solids were allowed to react with 4-bromomethylbenzylphosphonic acid, to thereby obtain an electrochromic compound (Ex.-10). The yield was 90%.

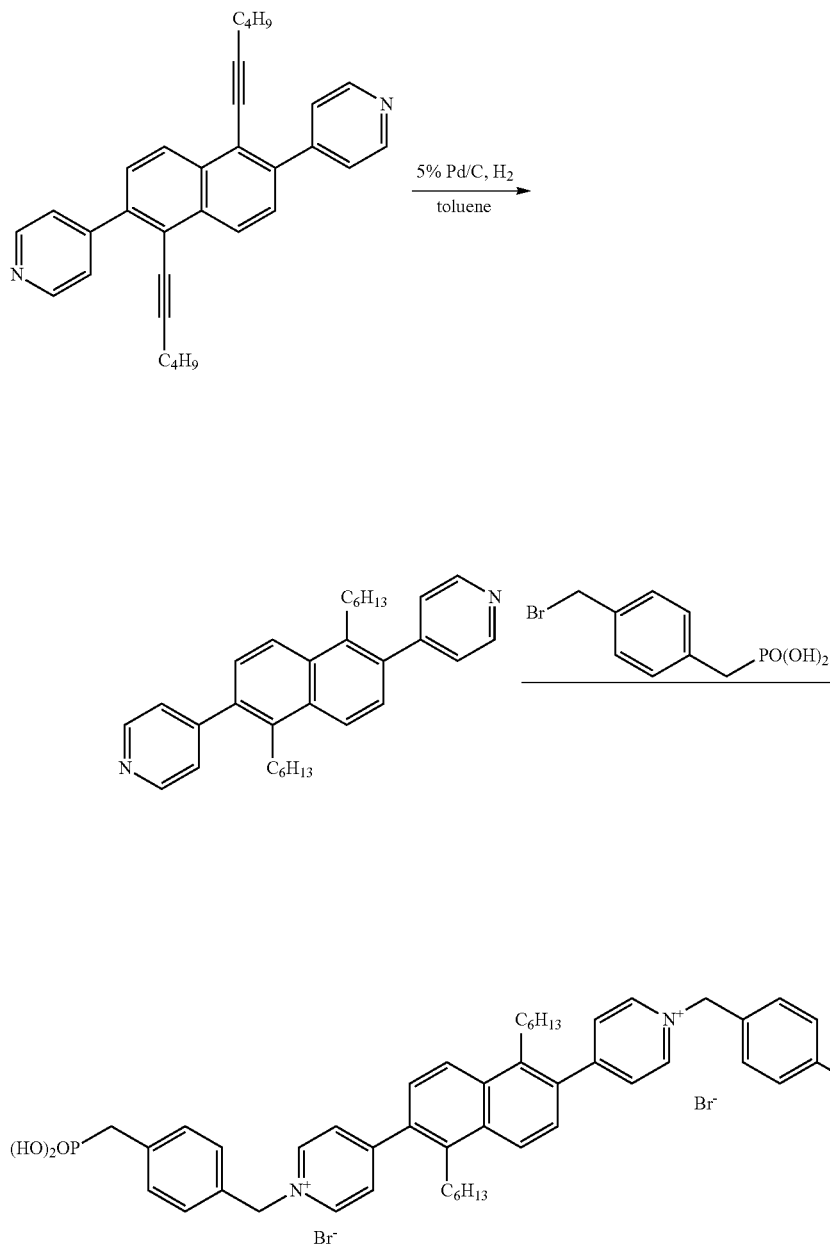

Example 11
An electrochromic compound (Ex.-11) was synthesized in the same manner as in Example 3, provided that 2,6-dibromo-1,5-dimethoxynaphthalene was replaced with 2,6-dibromo-1,5-di(2-ethylhexyloxy)naphthalene. The yield was 72%.
(Ex.-11)
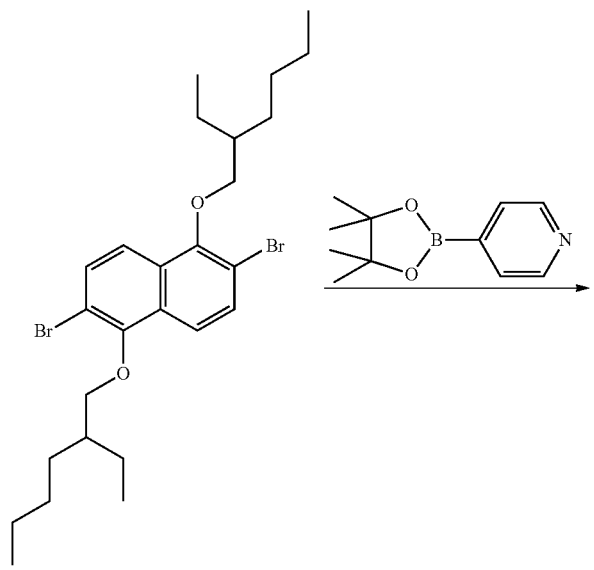
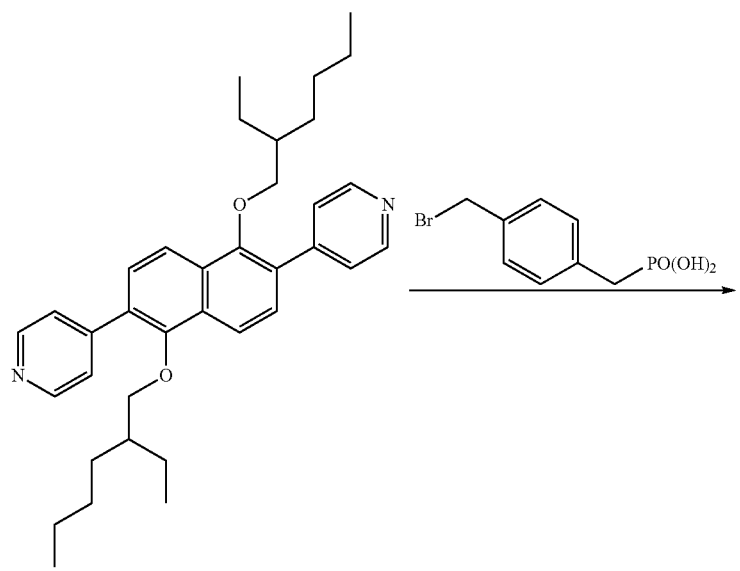

-continued
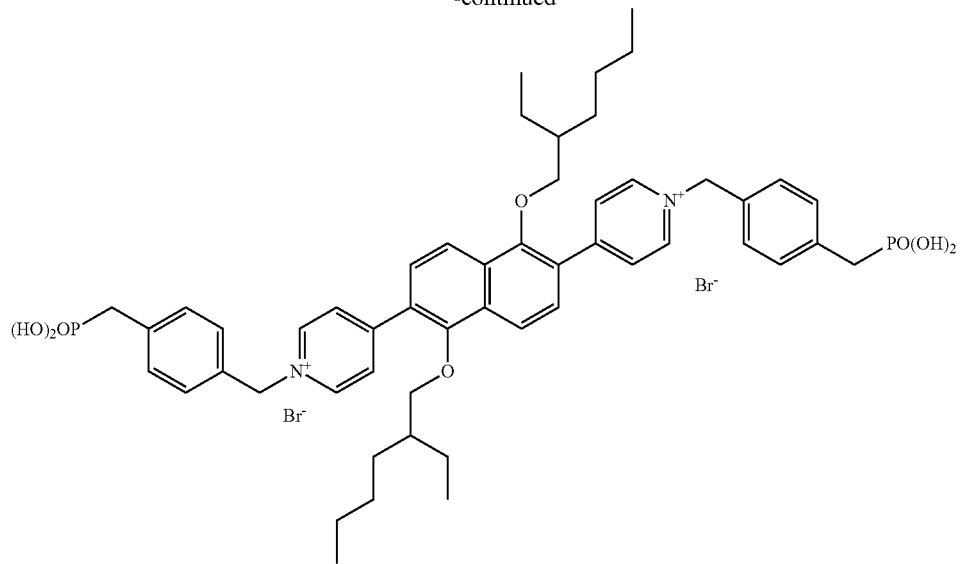
Example 12
An electrochromic compound (Ex.-12) was synthesized as yellow crystals in the same manner as in Example 3, provided that 2,6-dibromo-1,5-dimethoxynaphthalene was replaced with 3,7-dibromo-1,5-diphenylnaphthalene. The yield was 70%.
(Ex.-12)
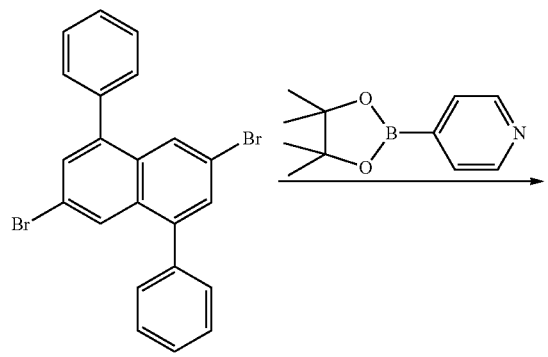
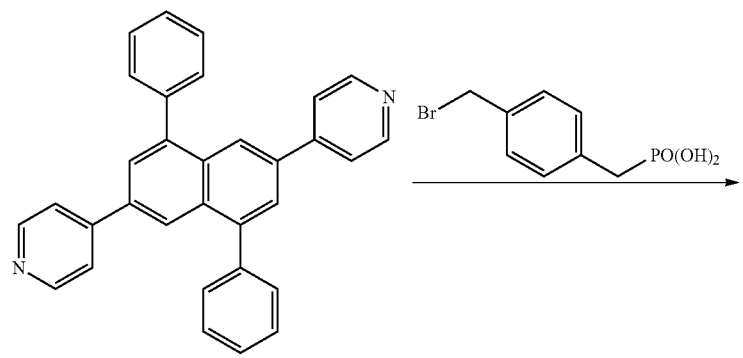

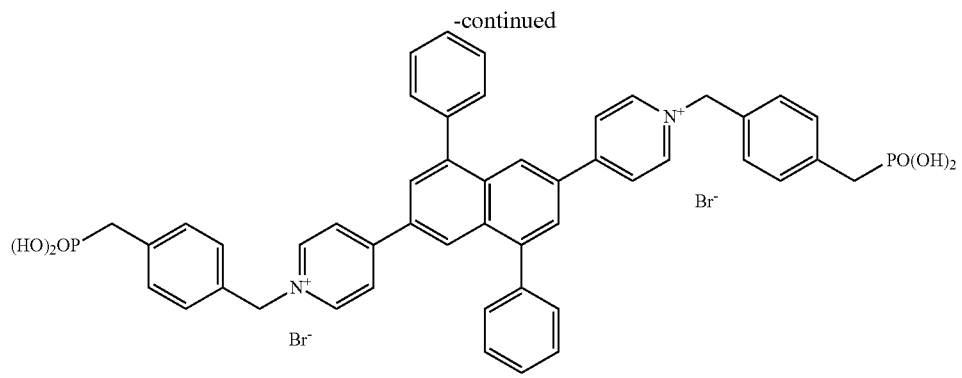

Example 13

A 50 mL-flask was charged with 0.400 g of 1,5-trifluoromethanesulfonyloxy-2,6-di(4-pyridyl)naphthalene, 0.315 g of 2-methoxyphenylboronic acid, 0.366 g of sodium carbonate, 80 mg of tetrakis triphenylphosphine palladium, 2 mL of water, and 10 mL of dioxane and was purged with argon. After the resulting mixture was stirred for 2 hours at 90° C., the mixture was cooled to room temperature. Chloroform was added to the mixture, and the resultant was subjected to filtration with CELITE. After washing the filtrate with water, the solvent was removed from the filtrate under the reduced pressure, and the residue was washed with ethyl acetate, to thereby obtain 0.205 g of colorless solids.

A 25 mL-flask was charged with 0.100 g of the above-obtained colorless solids, 0.160 g of 4-bromomethylbenzylphosphonic acid, and 3 mL of N,N-dimethylformamide (DMF), and the resulting mixture was stirred for 3 hours at 90° C. under the argon flow. To the resulting reaction solution, 2-propanol was added, to thereby precipitate yellow solids. The yellow solids were collected by filtration, and dried, to thereby obtain 0.179 g of an electrochromic compound (Ex.-13) as colorless crystals. The yield was 86%.

(Ex.-13)

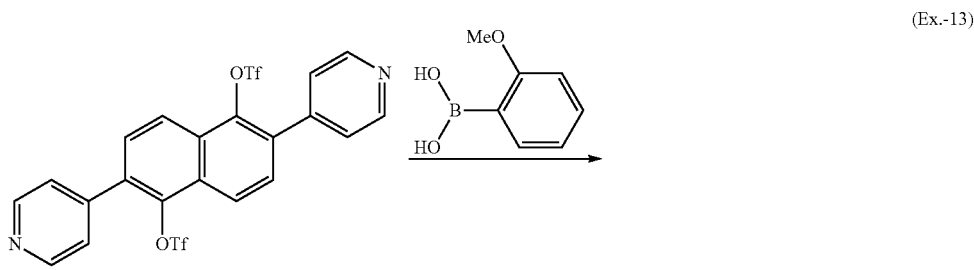

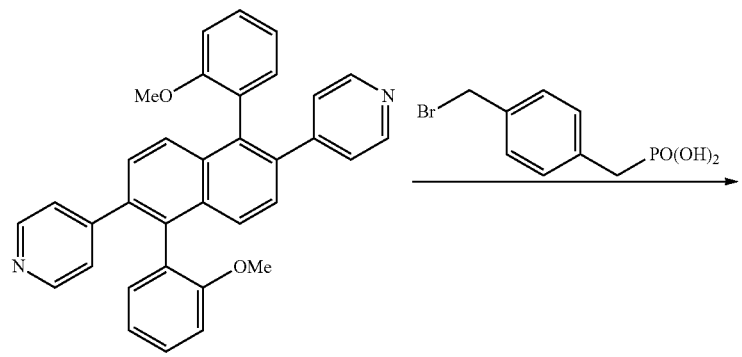

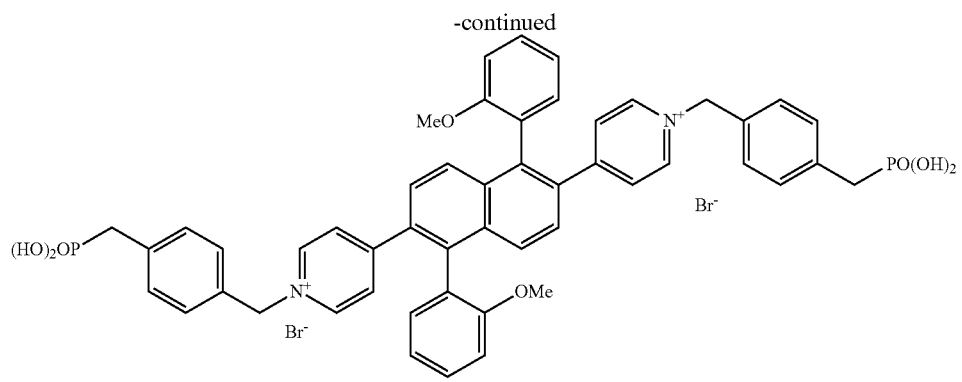
Example 14
An electrochromic compound (Ex.-14) (cream color crystals) was synthesized in the same manner as in Example 13, provided that 2-methoxyphenylboronic acid was replaced with 2,4-difluorophenylboronic acid. The yield was 67%.
(Ex.-14)
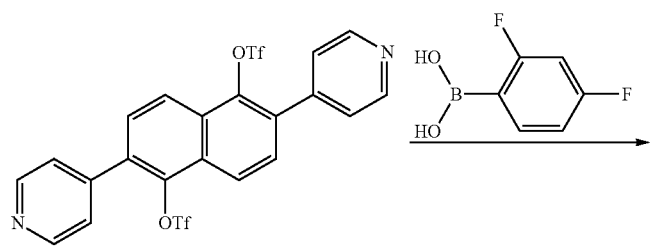
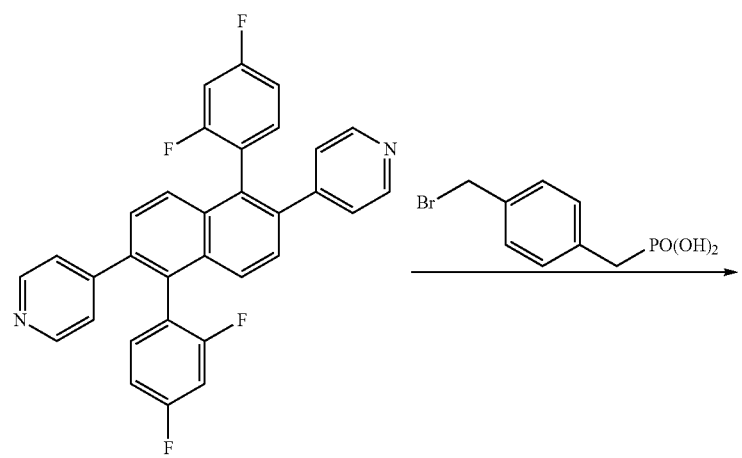

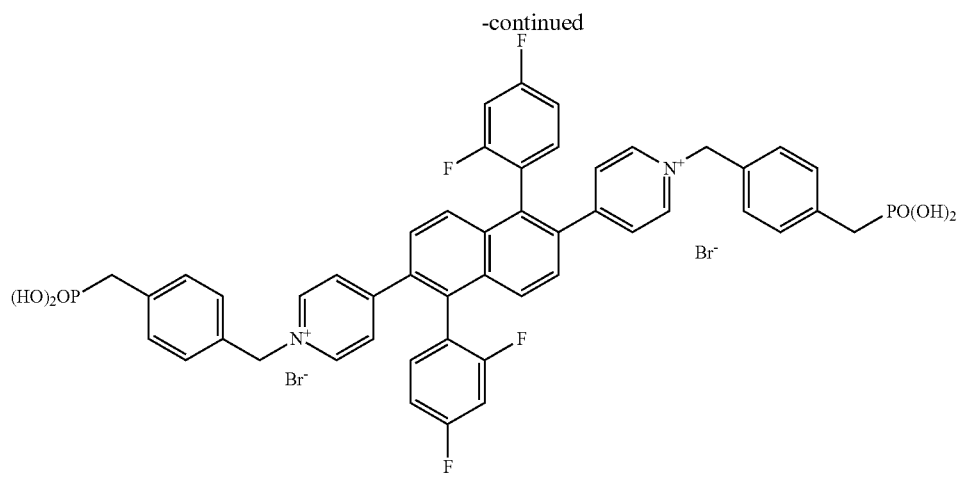

Example 15

A 50 mL-flask was charged with 0.300 g of 1,5-dihydroxy-2,6-di(4-pyridyl)naphthalene, 0.6 mL of pyridine, and 4 mL of tetrahydrofuran, and was purged with argon gas. The resulting mixture was cooled to 0° C., to which 0.54 mL of hexanoyl chloride was added dropwise. Thereafter, the resulting mixture was stirred for 2 hours at room temperature. The solvent was removed from the solution under reduced pressure, followed by purifying the residues by column chromatography, to thereby obtain 0.317 g of colorless solids.

A 25 mL-flask was charged with 0.23 g of the above-obtained colorless solids, 0.358 g of 4-bromomethylbenzylphosphonic acid and 4 mL of DMF, and the resulting mixture was stirred for 3 hours at 90° C. under the flow of argon gas. To the resulting reaction solution, 2-propanol was added to precipitate yellow solids. The yellow solids were collected through filtration, and dried, to thereby obtain 0.361 g of an electrochromic compound (Ex.-15) as yellow crystals.

(Ex.-15)

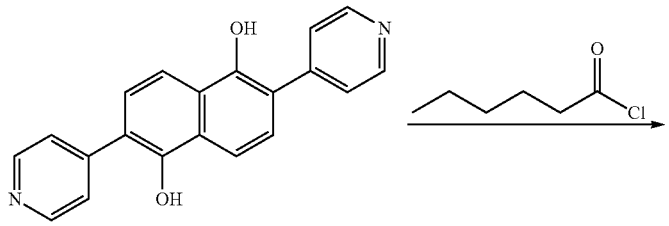

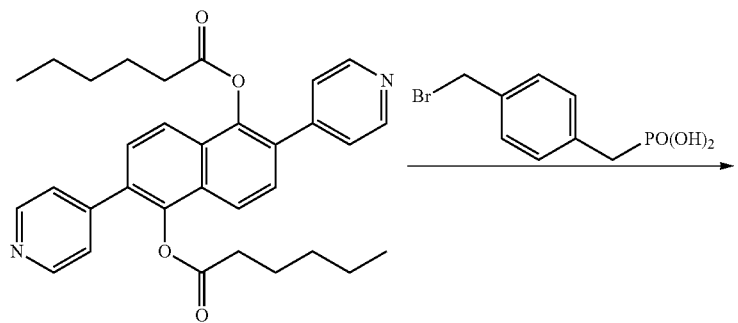

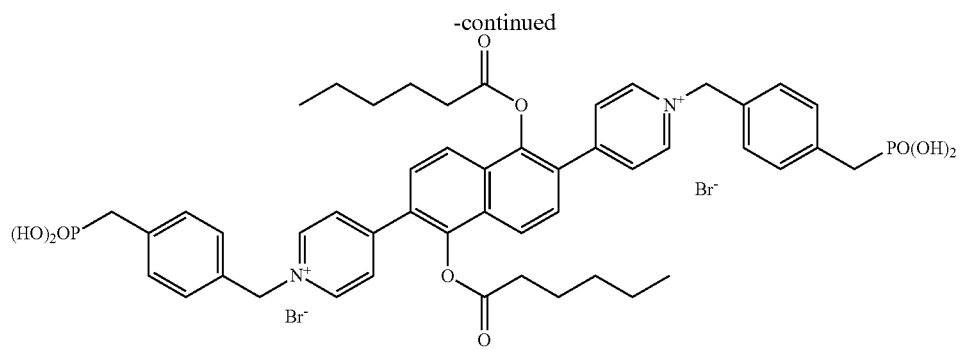

Example 16

An electrochromic display element was formed using each of electrochromic compounds synthesized in Examples 10 to 15 in the same manner as in Example 6. As for a counter electrode, a platinum electrode was used. As for a reference electrode, an Ag/Ag+ electrode (RE-7, manufactured by BAS Inc.) was used. A cell was filled with an electrolytic solution prepared by 0.1 M of tetrabutylammonium perchlorate in dimethyl sulfoxide. Light was applied to the quartz cell from a deuterium tungsten halogen light source (DH-2000, manufactured by Ocean Optics, Inc.). The transmitted light was detected by a spectrometer (USB4000, manufactured by Ocean Optics, Inc.), to measure the absorption spectrum. The absorption spectrums of the bleached state and colored state are presented in FIGS. 8 to 13.

When the voltage of −1.5 V was applied using a potentiostat (ALS-660C, manufactured by BAS Inc.), the maximum absorption wavelength was around 650 nm to around 700 nm, and the electrochromic display layer colored in vivid cyan.

Comparative Example 1

The following electrochromic compound (Comp.-1) was synthesized from 4,4'-bipyridine and 4-bromomethylbenzylphosphonic acid in accordance with the method described in Example 3.

Comparative Example 2

The following electrochromic compound (Comp.-2) was synthesized from 1,4-di(4-pyridyl)benzene and 4-bromomethylbenzylphosphonic acid in accordance with the method described in Example 3.

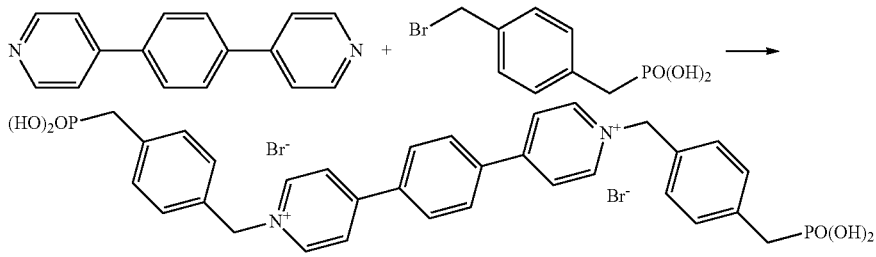

Comparative Example 3

The following electrochromic compound (Comp.-3) was synthesized from 4,4'-di(4-pyridyl)biphenyl and 4-bromomethylbenzylphosphonic acid in accordance with the method described in Example 3.

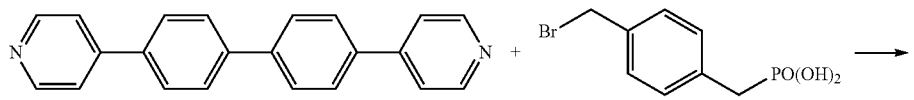

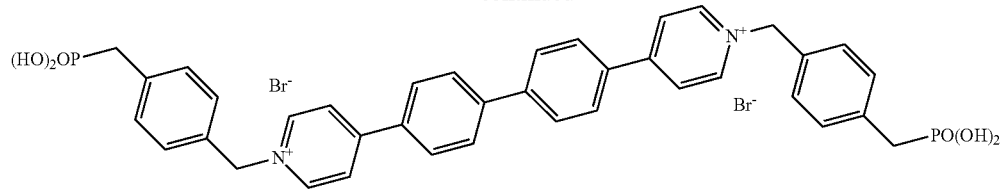

Comparative Example 4

The following electrochromic compound (Comp.-4) was synthesized using 2,7-dibromonaphthalene in accordance with the method described in Example 3.

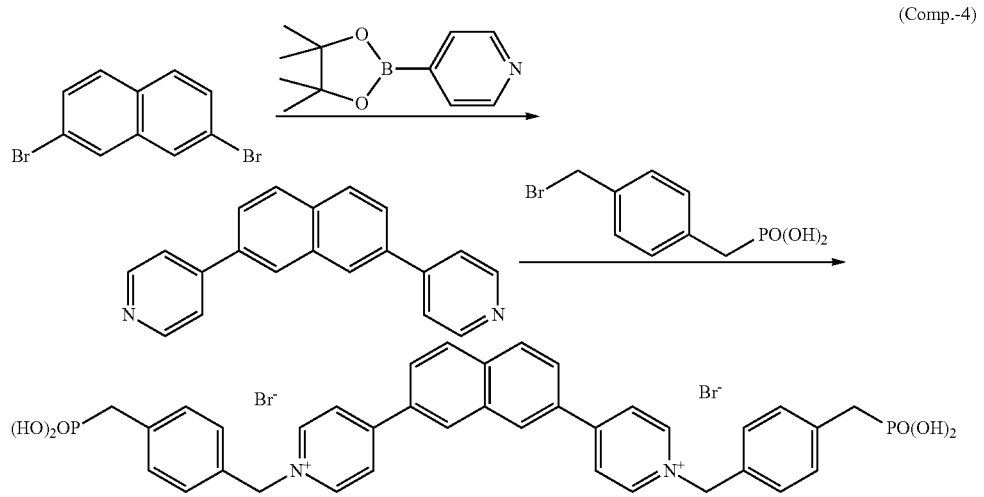

(Comp.-4)

Comparative Examples 5 to 8

Figure 14:
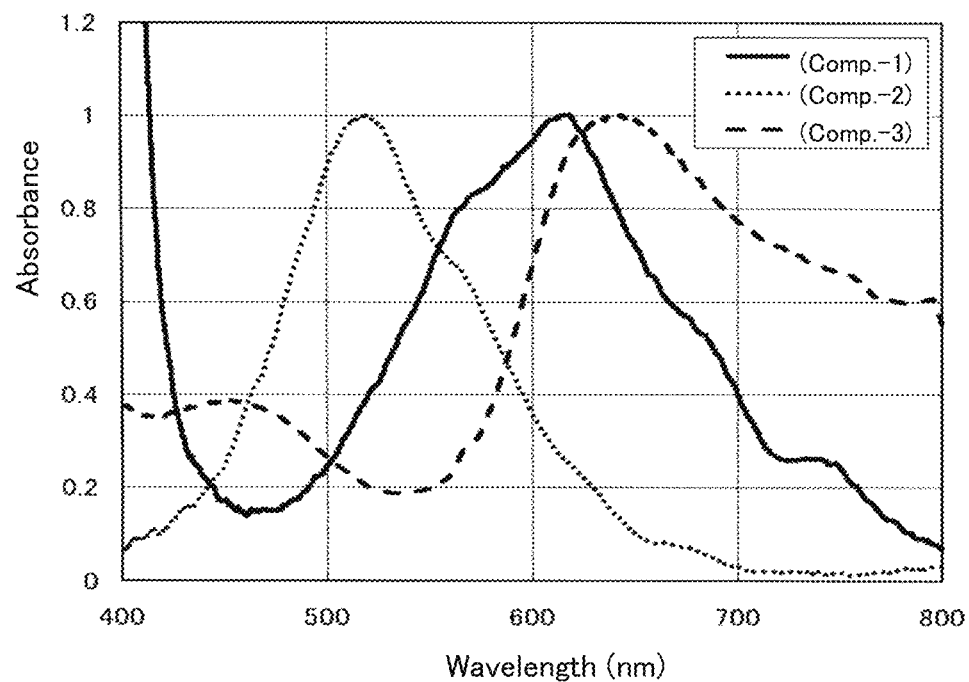
FIG. 14 is a diagram depicting absorption spectrums of the display electrodes of Comparative Examples 1 to 3, on each of which the electrochromic display layer is formed, in the colored state.

Using each of the electrochromic compounds synthesized in Comparative Examples 1 to 4, a display electrode, an electrochromic display layer, and an electrochromic display element were produced in the same manner as in (a) to (c) of Example 6. The absorption spectrums of the colored state of the electrochromic display elements producing using the comparative compounds (Comp.-1), (Comp.-2), and (Comp.-3) of Comparative Examples 1 to 3 are depicted in FIG. 14. Moreover, the absorption spectrums of the bleached and colored states of the electrochromic display element produced using the comparative compound (Comp.-4) of Comparative Example 4 are depicted in FIG. 15.

The compound (Comp.-1) and the compound (Comp.-2) depicted in FIG. 14 respectively colored in blue, and in red, and the both compounds did not color in cyan. Regarding the compound (Comp.-3), the color associated with the absorption band of 450 nm was mixed the color of the absorption band of 620 nm, and therefore the compound did not color in cyan.

Figure 15:
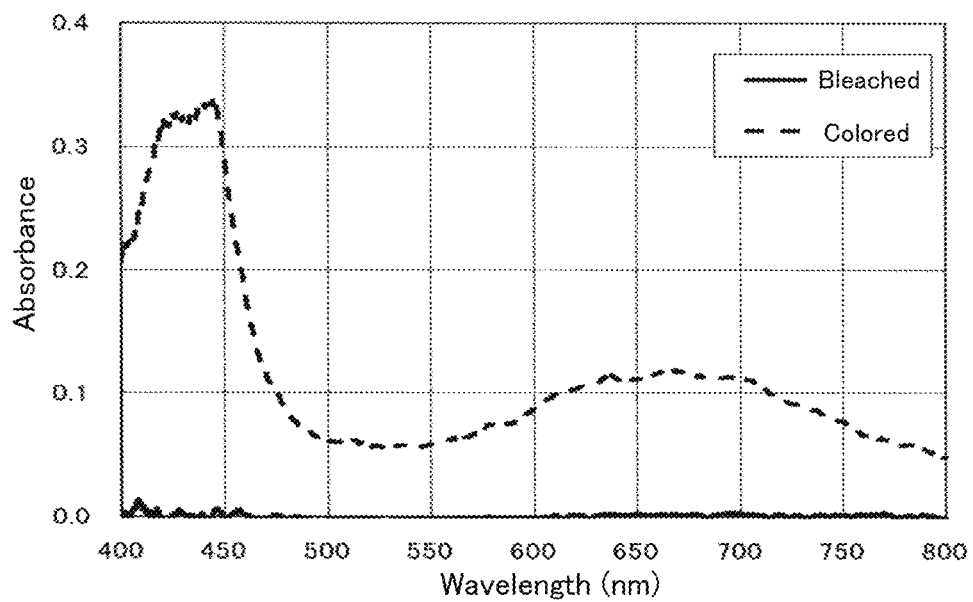
FIG. 15 is a diagram depicting absorption spectrums of the display electrode of Comparative Example 4, on which the electrochromic display layer is formed, in the bleached state and the colored state.

Regarding the compound (Comp.-4) depicted in FIG. 15, the absorption band of 450 nm was stronger than the absorption band adjacent to 650 nm. Therefore, the compound (Comp.-4) colored in yellow, not in cyan.

The display element, which has the electrochromic compound of the present invention, or the electrochromic composition, in which the electrochromic compound is bonded to or adsorbed on an electroconductive or semiconductive nano structure in a display layer, exhibits excellent a coloring or bleaching (coloring in cyan or bleaching the color) response to application of electric field, and also have excellent image retantiveness (maintaining memory).

Accordingly, the electrochromic compound of the present invention is effective for one of 3 primary colors required for realizing full-color, and the display element using such electrochromic compound is important as technologies of a rewritable paper-like device.

The embodiments of the present invention are, for example, as follows.

<1> An electrochromic compound, which is represented by the following general formula (I):

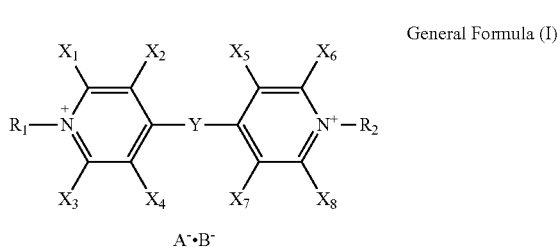

General Formula (I)

where $X_1$, $X_2$, $X_3$, $X_4$, $X_5$, $X_6$, $X_7$ and $X_8$ are each independently a hydrogen atom or a monovalent substituent; $R_1$ and $R_2$ are each independently a monovalent substituent; $A^-$ and $B^-$ are each independently a monovalent anion; and Y is represented by the following general formula (II) or (III):

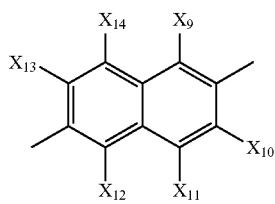

General Formula (II)

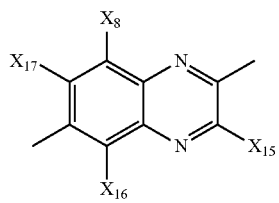

General Formula (III)

where $X_9$, $X_{10}$, $X_{11}$, $X_{12}$, $X_{13}$, $X_{14}$, $X_{15}$, $X_{16}$, $X_{17}$, and $X_{18}$ are each independently a hydrogen atom or a monovalent substituent.

<2> The electrochromic compound according to <1>, wherein the electrochromic compound is represented by the following general formula (IV):

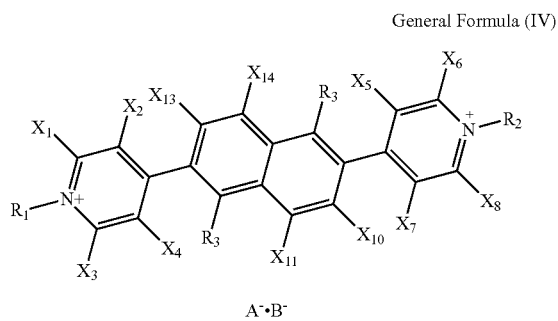

General Formula (IV)

$A^- \cdot B^-$ where $X_1$, $X_2$, $X_3$, $X_4$, $X_5$, $X_6$, $X_7$, $X_8$, $X_{10}$, $X_{11}$, $X_{13}$ and $X_{14}$ are each independently a hydrogen atom or a monovalent substituent; $R_3$ is a substituted or unsubstituted alkyl group, or a substituted or unsubstituted alkoxy group; $R_1$ and $R_2$ are each independently a monovalent substituent; and $A^-$ and $B^-$ are each independently a monovalent anion.

<3> The electrochromic compound according to any of <1> or <2>, wherein, in the general formula (I), $R_1$, or $R_2$, or both thereof has a functional group capable of directly or indirectly bonding to a hydroxyl group.

<4> The electrochromic compound according to <3>, wherein the functional group capable of directly or indirectly bonding to a hydroxyl group is one selected from the group consisting of a phosphonic acid group, a phosphoric acid group, a carboxyl group, a silyl group, and a silanol group.

<5> The electrochromic compound according to any of <3> or <4>, wherein the functional group capable of directly or indirectly bonding to a hydroxyl group is one selected from the group consisting of a phosphonic acid group, a trialkoxysilyl group, and a trihydroxysilyl group.

<6> The electrochromic compound according to any one of <1> to <5>, wherein $A^-$ and $B^-$ may be identical or different from each other, and are each selected from the group consisting of $Br^-$, $Cl^-$, $ClO_4^-$, $PF_6^-$, and $BF_4^-$.

<7> An electrochromic composition, containing:
an electroconductive or semiconductive nano structure; and
the electrochromic compound according to any one of <1> to <6>, which is bonded to or adsorbed on the nano structure.

<8> The electrochromic composition according to <7>, wherein the electroconductive or semiconductive nano structure is composed of metal oxide particles, and wherein the metal oxide particles are at least one selected from the group consisting of titanium oxide, zinc oxide, tin oxide, alumina, zirconium oxide, iron oxide, magnesium oxide, indium oxide, and tungsten oxide.

<9> The electrochromic composition according to <8>, wherein the metal oxide particles have an average primary particle diameter of 30 nm or smaller.

<10> A display element, containing:
a display electrode;
a counter electrode provided to face the display electrode and to be spaced from the display electrode;
an electrolyte provided between the display electrode and the counter electrode; and
a display layer provided on a surface of the display electrode, which surface faces the counter electrode,
wherein the display layer contains the electrochromic compound according to any one of <1> to <6>, or the electrochromic composition according to any one of <7> to <9>.

REFERENCE SIGNS LIST 1 display electrode
2 counter electrode
3 electrolyte
4a electrochromic compound
4b oxidation-reduction coloring section
4c adsorbing group (bonding group)
4d spacer section
4e electrochromic composition
5 display layer
6 white reflecting layer
10, 20, 30 display element

The invention claimed is:
1. A display element, comprising:
a display electrode;
a counter electrode provided to face the display electrode and to be spaced from the display electrode;
an electrolyte provided between the display electrode and the counter electrode; and
a display layer provided on a surface of the display electrode, wherein the surface faces the counter electrode,
wherein the display layer comprises an electrochromic compound represented by the following Formula (I):

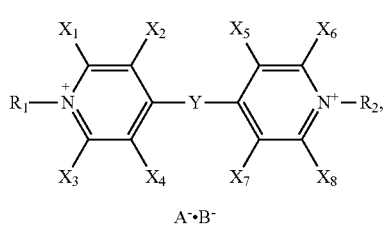

Formula (I)

A⁻·B⁻ wherein $X_1$, $X_2$, $X_3$, $X_4$, $X_5$, $X_6$, $X_7$ and $X_8$ are each independently a hydrogen atom or a monovalent substituent; $R_1$ and $R_2$ are each independently a monovalent substituent; $A^-$ and $B^-$ are each independently a monovalent anion; and Y is represented by the following Formula (II) or (III):

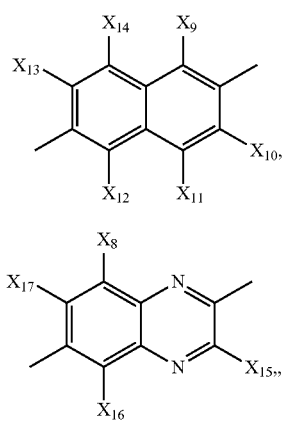

Formula (II)

Formula (III)

wherein $X_9$, $X_{10}$, $X_{11}$, $X_{12}$, $X_{13}$, $X_{14}$, $X_{15}$, $X_{16}$, $X_{17}$, and $X_{18}$ are each independently a hydrogen atom or a monovalent substituent, and wherein $R_1$, $R_2$ or both comprise a functional group capable of directly or indirectly bonding to a hydroxyl group.

2. The display element of claim 1, wherein the display layer comprises an electrochromic composition comprising the electrochromic compound and an electroconductive or semiconductive nanostructure, wherein the electrochromic compound is bonded to or adsorbed on the nanostructure.

3. The display element of claim 2, wherein the electroconductive or semiconductive nanostructure is composed of metal oxide particles, and wherein the metal oxide particles are at least one selected from the group consisting of titanium oxide, zinc oxide, tin oxide, alumina, zirconium oxide, iron oxide, magnesium oxide, indium oxide, and tungsten oxide.

4. The display element of claim 3, wherein the metal oxide particles have an average primary particle diameter of 30 nm or smaller.

5. The display element of claim 1, wherein an electrochromic compound is represented by the following Formula (IV):

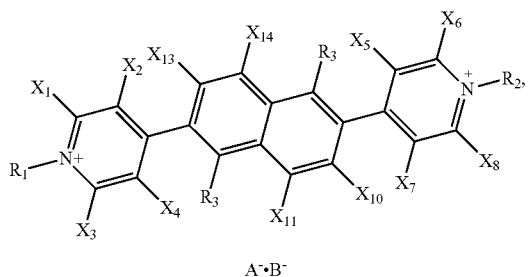

A⁻·B⁻ wherein $X_1$, $X_2$, $X_3$, $X_4$, $X_5$, $X_6$, $X_7$, $X_8$, $X_{10}$, $X_{11}$, $X_{13}$ and $X_{14}$ are each independently a hydrogen atom or a monovalent substituent; $R_3$ is a substituted or unsubstituted alkyl group, or a substituted or unsubstituted alkoxy group; $R_1$ and $R_2$ are each independently a monovalent substituent; and $A^-$ and $B^-$ are each independently a monovalent anion.

6. The display element of claim 1, wherein the monovalent anions $A^-$ and $B^-$ are each independently Br ion (Br⁻), Cl ion (Cl⁻), $ClO_4$ ion ($ClO_4^-$), $PF_6$ ion ($PF_6^-$), or $BF_4$ ion ($BF_4^-$).

7. The display element of claim 2, wherein the electrochromic compound comprises a sulfonic acid group, a phosphoric acid group, or a carboxyl group as a binding or adsorbing structure such that the electrochromic compound forms a complex with the nanostructure.

8. The display element of claim 2, wherein, when the electrochromic compound comprises a silyl group or a silanol group, the electrochromic compound bonds to the nanostructure through a siloxane bond, which forms a bond between the electrochromic compound and the nanostructure.

9. The display element of claim 2, wherein a specific surface area of the nanostructure is 100 m²/g or greater.

10. The display element of claim 1, further comprising a white reflecting layer formed of white pigment particles provided on a surface of the counter electrode at a side of the display electrode.

11. The display element of claim 1, wherein the display electrode is made from a transparent electric conductive substrate which is a substrate comprising a transparent electric conductive film coated on a glass or a plastic film.

12. The display element of claim 1, wherein the display electrode is made from a transparent electric conductive material comprising at least one selected from the group consisting of tin-doped indium oxide, fluorine-doped tin oxide, antimony-doped tin oxide, indium oxide, tin oxide, and zinc oxide.

13. The display element of claim 1, wherein the electrolyte is at least one selected from the group consisting of a fluid electrolyte, a gel electrolyte, and a solid electrolyte.

14. The display element of claim 10, wherein the white pigment particles are selected from the group consisting titanium oxide, aluminum oxide, zinc oxide, silicon oxide, cesium oxide, yttrium oxide, and a combination thereof.

* * * * *